(12) United States Patent
Lin et al.

(10) Patent No.: US 12,318,496 B2
(45) Date of Patent: Jun. 3, 2025

(54) MEDICAL DEVICES AND COMPOMENTS THEREOF

(71) Applicant: SHANGHAI UNITED IMAGING HEALTHCARE CO., LTD., Shanghai (CN)

(72) Inventors: Yangyang Lin, Shanghai (CN); Yanfeng Du, Shanghai (CN); Yifeng Jiang, Shanghai (CN); Pei Zhou, Shanghai (CN); Tingting Wu, Shanghai (CN); Daheng Chen, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 754 days.

(21) Appl. No.: 17/644,584

(22) Filed: Dec. 16, 2021

(65) Prior Publication Data

US 2022/0193284 A1    Jun. 23, 2022

(30) Foreign Application Priority Data

Dec. 16, 2020  (CN) .......................... 202023031757.7
Dec. 16, 2020  (CN) .......................... 202023036564.0
Dec. 16, 2020  (CN) .......................... 202023045076.6
Dec. 16, 2020  (CN) .......................... 202023045078.5

(51) Int. Cl.
*A61L 2/10*    (2006.01)
*A61B 6/00*    (2006.01)
(Continued)

(52) U.S. Cl.
CPC .............. *A61L 2/10* (2013.01); *A61B 6/4435* (2013.01); *A61G 3/008* (2013.01); *A61G 10/02* (2013.01); *A61L 2/14* (2013.01); *A61L 2/202* (2013.01); *A61L 2/22* (2013.01); *A61L 2/24* (2013.01); *A61L 2/26* (2013.01); *A61L 9/015* (2013.01); *A61L 9/14* (2013.01); *A61L 9/20* (2013.01); *A61L 9/22* (2013.01); *A61L 2202/11* (2013.01); *A61L 2202/14* (2013.01);
(Continued)

(58) Field of Classification Search
CPC ... A61L 2/10; A61L 2/14; A61L 2/202; A61L 2/22; A61L 2/24; A61L 2/26; A61L 9/015; A61L 9/14; A61L 9/20; A61L 9/22; A61L 2202/11; A61L 2202/14; A61L 2202/24; A61L 2202/25; A61L 2209/111; A61L 2209/14; A61L 2209/212; A61B 6/4435; A61G 3/008; A61G 10/02
See application file for complete search history.

(56) References Cited

U.S. PATENT DOCUMENTS

2021/0350912 A1* 11/2021 Shiroishi ................... A61B 6/54
2022/0047229 A1*  2/2022 Takata ..................... A61B 6/0414
2022/0193281 A1*  6/2022 Dencovski ................ A61L 9/20

FOREIGN PATENT DOCUMENTS

CN          213395746 U     6/2021

* cited by examiner

*Primary Examiner* — Dani Fox
*Assistant Examiner* — Fani Polyzos Boosalis
(74) *Attorney, Agent, or Firm* — METIS IP LLC

(57) ABSTRACT

The present disclosure provides a medical device. The medical device may include a gantry, a table, and one or more disinfection devices. The gantry may include a bore configured to accommodate an object for scan. The table may be configured to support the object and move the object into the bore. The one or more disinfection devices may be configured for disinfection.

20 Claims, 18 Drawing Sheets

(51) Int. Cl.
*A61G 3/00* (2006.01)
*A61G 10/02* (2006.01)
*A61L 2/14* (2006.01)
*A61L 2/20* (2006.01)
*A61L 2/22* (2006.01)
*A61L 2/24* (2006.01)
*A61L 2/26* (2006.01)
*A61L 9/015* (2006.01)
*A61L 9/14* (2006.01)
*A61L 9/20* (2006.01)
*A61L 9/22* (2006.01)

(52) U.S. Cl.
CPC ....... *A61L 2202/24* (2013.01); *A61L 2202/25* (2013.01); *A61L 2209/111* (2013.01); *A61L 2209/14* (2013.01); *A61L 2209/212* (2013.01)

600

Side View　　　　　　　　　　Front View

1100

1200

MEDICAL DEVICES AND COMPOMENTS THEREOF

CROSS-REFERENCE TO RELATED APPLICATIONS

This application claims priority of Chinese Patent Application No. 202023045078.5, filed on Dec. 16, 2020, Chinese Patent Application No. 202023045076.6, filed on Dec. 16, 2020, Chinese Patent Application No. 202023031757.7, filed on Dec. 16, 2020, and Chinese Patent Application No. 202023036564.0, filed on Dec. 16, 2020, the contents of each of which are hereby incorporated by reference.

TECHNICAL FIELD

The present disclosure generally relates to medical devices, and more particularly, to a display apparatus for a medical device provided with a disinfection device.

BACKGROUND

Medical devices such as a computed tomography (CT) device, a radiotherapy device, etc., play a very important role in disease diagnosis and treatment in modern times. Generally, the use of a medical device for disease diagnosis and treatment is carried out in a confined space. After scanning or treating a patient infected with an infectious disease, if the medical device cannot be disinfected in time, it is easily to cause cross-infection between different patients and/or medical staff (e.g., doctors). However, a traditional medical device is not equipped with a disinfection device, and the disinfection of the traditional medical device requires a professional staff to move the disinfection device from other places to disinfect the medical device, which is time-consuming and laborious. Therefore, it is desirable to develop a medical device provided with a disinfection device to provide a safe and reliable environment for users.

SUMMARY

According to an aspect of the present disclosure, a medical device is provided. The medical device may include a gantry, a table, and one or more disinfection devices. The gantry may include a bore configured to accommodate an object for scan. The table may be configured to support the object and move the object into the bore. The one or more disinfection devices may be configured for disinfection.

In some embodiments, at least one of the one or more disinfection devices may be arranged on the table.

In some embodiments, the at least one of the one or more disinfection devices may be foldable or retractable.

In some embodiments, the at least one of the one or more disinfection devices may be arranged on a housing of the gantry.

In some embodiments, the bore may include a first opening and a second opening, and the at least one of the one or more disinfection devices may be arranged at an end portion of the housing having the first opening or the second opening.

In some embodiments, the at least one of the one or more disinfection devices may be arranged at a position of the housing corresponding to a top or bottom end of the bore.

In some embodiments, at least one of the one or more disinfection devices may be arranged on the gantry or a component supported by the gantry.

In some embodiments, a housing of the gantry may be provided with a door to allow a disinfection medium of the at least one of the one or more disinfection devices to pass through when the door is in an open state.

In some embodiments, a disinfection medium of the at least one of the one or more disinfection devices may penetrate the housing to the bore.

In some embodiments, at least a part of the housing may be made of one of quartz glass, polymethyl methacrylate, and polycarbonate.

In some embodiments, the medical device may further include a table controller configured to control the table to move into the bore after at least one of the one or more disinfection devices performs disinfection for a preset time period.

In some embodiments, the one or more disinfection devices may include at least one of an ultraviolet disinfection device, a plasma disinfection device, an atomization disinfection device, or an ozone disinfection device.

In some embodiments, the medical device may further include a radiation source and a detector mounted on the gantry. A housing of the gantry may form a cavity configured to accommodate the radiation source and the detector, and at least one of the one or more disinfection devices may be located in the cavity.

In some embodiments, the medical device may further include an air inlet and an air outlet both arranged on the housing. At least one of the air inlet or the air outlet may be provided with one or more filtering devices in the cavity.

In some embodiments, at least one of the one or more filtering devices may be arranged at the air inlet. The at least one of the one or more disinfection devices may be arranged between the at least one of the one or more filtering devices and the air inlet.

In some embodiments, at least one of the one or more filtering devices may be arranged at the air outlet. The at least one of the one or more filtering devices may be arranged between the at least one or more disinfection devices and the air outlet.

In some embodiments, the one or more filtering devices may include a first filtering device, a second filtering device, and a third filtering device. The first filtering device may be arranged at the air inlet. The second filtering device may be arranged at the air outlet. The third filtering device may be arranged between the first filtering device and the second filtering device. The at least one of the one or more disinfection devices may be arranged between the first filtering device and the third filtering device or arranged between the second filtering device and the third filtering device.

In some embodiments, the one or more filtering devices may include at least one of a high efficiency particulate air (HEPA) filter, an activated carbon filter, a photocatalyst filter, or an electrostatic adsorption filter.

In some embodiments, the one or more disinfection devices may include a first disinfection device and a second disinfection device. An orientation of the first disinfection device may be different from an orientation of the second disinfection device.

In some embodiments, the medical device may further include a monitoring device configured to acquire monitoring information associated with at least one of the medical device or the object and a control device configured to prevent at least one of the one or more disinfection devices from disinfecting the medical device in response to the monitoring information indicating that at least one object is within a preset range of the medical device.

In some embodiments, the medical device may further include an acquisition module configured to acquire information associated with at least one of the medical device or the object and a control device. The control device may be configured to determine that the medical device needs to be disinfected when the information associated with the at least one of the medical device or the object satisfies a compliance condition and generate a control instruction in response to determining that the medical device needs to be disinfected.

In some embodiments, the control instruction may include a disinfection instruction to control at least one of the one or more disinfection devices to perform disinfection.

In some embodiments, the control instruction may include a scan control instruction for restricting at least part of functions of the medical device to work.

In some embodiments, the control device may be further configured to control at least one of the one or more disinfection devices to perform disinfection in response to receiving a disinfection instruction generated based on an input by a user that instructs to perform disinfection.

In some embodiments, the medical device may further include an alarm device. The control device may further be configured to trigger the alarm device to generate an alarm signal indicating that the medical device needs to be disinfected in response to determining that the information associated with the at least one of the medical device or the object satisfies the compliance condition.

In some embodiments, the alarm device may be further configured to obtain disinfection progress information. The control device may be further configured to allow the at least part of functions of the medical device to work in response to the disinfection progress information indicating that the disinfection is completed.

In some embodiments, the medical device may further include a medical device controller configured to determine a state of the medical device. The control device may determine whether the medical device needs to be disinfected based on the information associated with the medical device or the object and the state of the medical device.

In some embodiments, the acquisition module may be connected with a temperature measurement device. The temperature measurement device may be configured to acquire temperature information of one or more objects within a first range of the medical device. The compliance condition may include that at least one object of the one or more objects has a temperature greater than a temperature threshold.

In some embodiments, the acquisition module may be connected with a medical database. The medical database may include historical medical information of the object.

In some embodiments, the acquisition module may be connected with a monitoring device. The monitoring device may be configured to capture monitoring information of a second range of the medical device.

In some embodiments, the monitoring device may include an imaging acquisition device or an audio acquisition device.

In some embodiments, the medical device may include a computed tomography (CT) device. The acquisition module may be connected with an image processing device of the CT device to acquire image information of a region of interesting (ROI) of the object.

According to another aspect of the present disclosure, an air purification device is provided. The air purification device may be arranged in a medical system including a medical cabin configured to accommodate medical resources. The air purification device may include one or more draught fans, one or more air inlets, one or more filtering devices, one or more disinfection devices, and one or more air outlets. At least one of the one or more filtering devices and at least one of the one or more disinfection devices may be arranged between at least one of the one or more air inlets and at least one of the one or more air outlets.

In some embodiments, the at least one of the one or more air inlets and the at least one of the one or more air outlets may be arranged on different sidewalls of the air purification device or a same sidewall of the air purification device.

In some embodiments, the at least one of the one or more air outlets may be provided with an air flow direction control device configured to control airflow in a first direction from the air purification device to the medical cabin and a second direction from the air purification device to the outside of the medical cabin.

In some embodiments, the one or more air outlets may include a first air outlet and a second air outlet. An air flow direction of the first air outlet may be from the air purification device to the medical cabin, and an air flow direction of the second air outlet may be from the air purification device to the outside of the medical cabin.

In some embodiments, the air purification device may further include a dust-proof net arranged between one of the one or more air inlets and at least one of the one or more filtering devices.

In some embodiments, the one or more filtering devices may include a first filtering device configured to filter particles of more than 5 μm.

In some embodiments, the one or more filtering devices may further include a second filtering device arranged at an air outflow side of the first filtering device. The second filtering device may be configured to filter particles of more than 1 μm.

In some embodiments, the one or more filtering devices may further include an activated carbon filter arranged between the first filtering device and the second filtering device.

In some embodiments, the one or more disinfection devices may include at least one of an ultraviolet disinfection device, a plasma disinfection device, an atomization disinfection device, or an ozone disinfection device.

In some embodiments, the air purification device may be mechanically arranged on a top surface of the medical cabin, a bottom surface of the medical cabin, or a sidewall of the medical cabin.

According to yet another aspect of the present disclosure, a medical system is provided. The medical system may include a medical cabin configured to accommodate medical resources. The medical cabin may include an operating room and an examination room equipped with a medical device. At least one of the operating room or the examination room may be equipped with an air purification device. The air purification device may include one or more draught fans, one or more air inlets, one or more filtering devices, one or more disinfection devices, and one or more air outlets. At least one of the one or more filtering devices and at least one of the one or more disinfection devices may be arranged between at least one of the one or more air inlets and at least one of the one or more air outlets.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
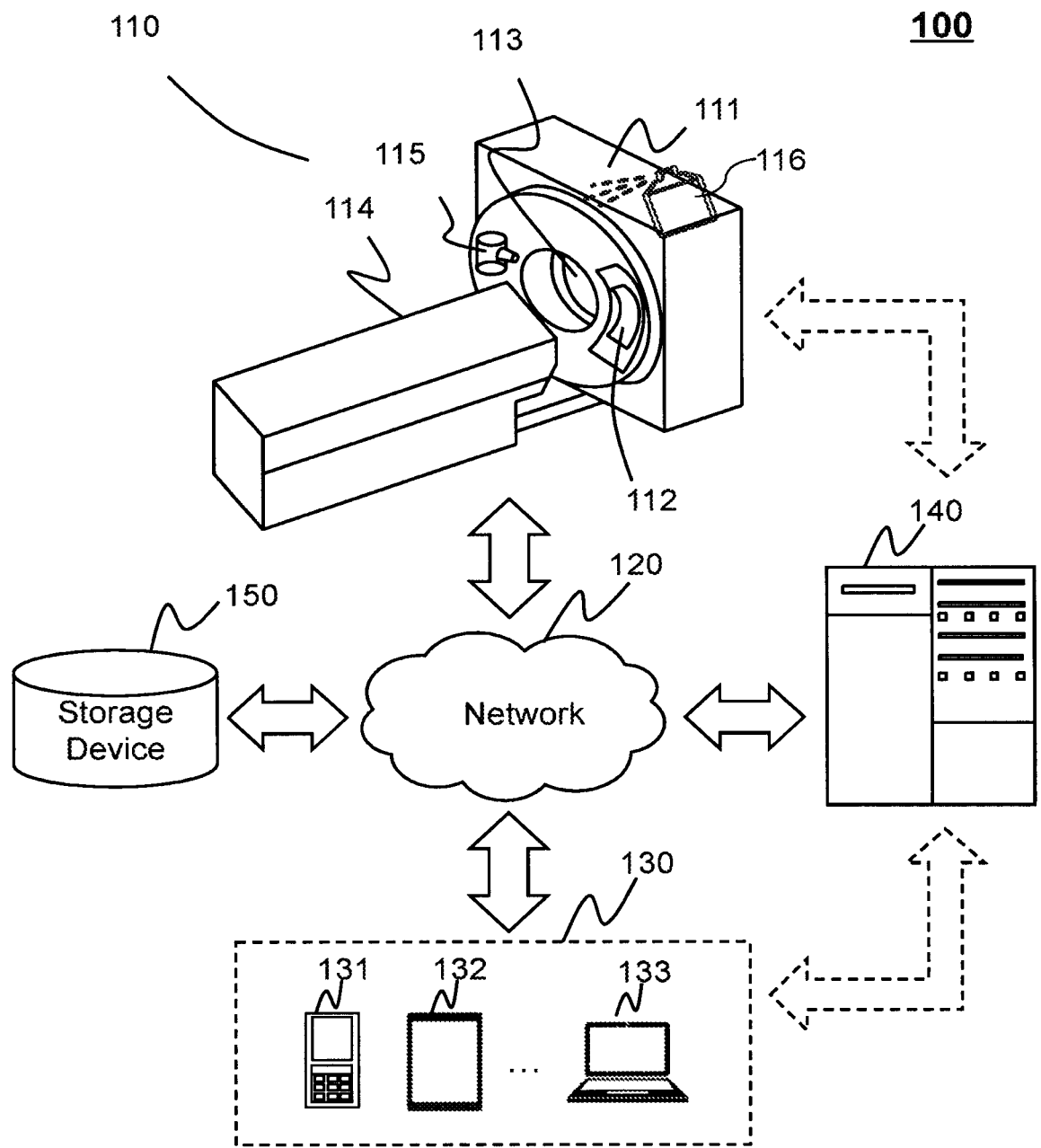
FIG. 1 is a schematic diagram illustrating an exemplary medical system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or maybe invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," "disposed," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent"). In some embodiments, engine, module, or block is referred to as being "on," "connected to," or "coupled to," another unit, engine, module, or block, it may communicate with the other unit, engine, module, or block. As used herein, the term "and/or" includes any and all combinations of one or more of the associated listed items.

It should also be understood that terms such as "top," "bottom," "upper," "lower," "vertical," "lateral," "above," "below," "upward(s)," "downward(s)," "left-hand side," "right-hand side," "left," "right," "horizontal," and other such spatial reference terms are used in a relative sense to describe the positions or orientations of certain surfaces/parts/components of a device with respect to other such features of the device when the device is in a normal operating position and may change if the position or orientation of the device changes.

An aspect of the present disclosure relates to medical devices. The medical device may include a gantry, a table, and one or more disinfection devices. The gantry may include a bore configured to accommodate an object for scan. The table may be configured to support the object and move the object into the bore. The disinfection device(s) may be configured for disinfection. For example, the disinfection device(s) may distinct the table, the bore, or a space in the gantry. As another example, the disinfection device(s) may disinfect a space (e.g., an examination room) where the medical device is located. Since the disinfection device(s) are arranged on the medical device, no need for peripheral devices (e.g., a suspension facility, a robot, etc.), which reduces space occupied by other peripheral devices, simplifies the installation of the disinfection device(s), and improves user experience. In addition, the disinfection device(s) may be connected with a control device configured to configured control the disinfection device(s), which simplifies disinfection operations, and is convenient for a user to operate. For example, the user may send a control instruction to the control device via a terminal device to turn on/off the disinfection device(s).

In some embodiments, the medical device may further include an acquisition module and a control device. The acquisition module may be configured to acquire information associated with the medical device and/or the object. The control device may be configured to determine whether the medical device needs to be disinfected based on the information associated with the medical device and/or the object and generate a control instruction in response to determining that the medical device needs to be disinfected. By using the information associated with the medical device and/or the object, whether the medical device needs to be disinfected may be determined in time. In such cases, the chance of the medical device being exposed to a virus space may be reduced and the probability of cross-infection between different patients and/or medical staff may be reduced.

Another aspect of the present disclosure relates to air purification devices. The air purification device may be arranged in a medical system including a medical cabin configured to accommodate medical resources. The air purification device may include a draught fan, one or more air inlets, one or more filtering devices, one or more disinfection devices, and one or more air outlets. At least one of the filtering device(s) and at least one of the disinfection device(s) may be arranged between one of the air inlet(s) and one of the air outlet(s). Accordingly, the air purification device may continuously suck air in the medical cabin into the interior of the air purification device through the air inlet(s). The air in the air purification device may be quickly filtered and disinfected, and then discharged from the air purification device to the medical cabin through the air outlet(s). Thus, the air in the medical cabin can be cleaned, so as to avoid cross-infection between patients and/or medical staff.

FIG. 1 is a schematic diagram illustrating an exemplary medical system according to some embodiments of the present disclosure. In some embodiments, the medical system 100 may be applied to a medical imaging and/or treatment system, such as a computed tomography (CT) system, a positron emission tomography (PET) system, a single-photon emission computed tomography (SPECT)

system, a magnetic resonance imaging (MRI) system, a digital radiography (DR) device, a radiotherapy system, a CT-PET system, a CT-MRI system, or the like, or a combination thereof.

As illustrated in FIG. 1, the medical system 100 may include a medical device 110, a network 120, a terminal device 130, a processing device 140, and a storage device 150. The components in the medical system 100 may be connected in one or more of various ways. Merely by way of example, the medical device 110 may be connected to the processing device 140 through the network 120. As another example, the medical device 110 may be connected to the processing device 140 directly as indicated by the bi-directional arrow in dotted lines linking the medical device 110 and the processing device 140. As a further example, the storage device 150 may be connected to the processing device 140 directly or through the network 120. As still a further example, the terminal device 130 may be connected to the processing device 140 directly (as indicated by the bi-directional arrow in dotted lines linking the terminal device 130 and the processing device 140) or through the network 120.

In some embodiments, the medical device 110 may include an imaging device and/or a treatment device. For example, the medical device 110 may include a computed tomography (CT) device, a positron emission tomography (PET) device, a single-photon emission computed tomography (SPECT) device, a magnetic resonance imaging (MRI) device, a radiotherapy device, a CT-PET device, a CT-MRI device, an image-guided radiation therapy (IGRT) device, or the like, or any combination thereof. For illustration purposes, an imaging device (e.g., a CT device) may be taken as an exemplary medical device 110 in the present disclosure. The imaging device may be configured to scan an object and generate imaging data used to generate one or more images relating to the object.

The imaging device 110 may include a gantry 111, a detector 112, a detecting region 113, a table 114, a radiation source 115, one or more disinfection devices 116, or any other components. The gantry 111 may be configured to provide support for other components (e.g., the radiation source 115, the detector(s) 112, the disinfection device 116, etc.) of the medical device 110. In some embodiments, the gantry 111 may include a main frame, a frame base, a front cover, and a rear cover (not shown). The frame base may support the front cover, the main frame, and/or the rear cover. In some embodiments, the front cover may be connected with the frame base vertically. The main frame may be arranged at a side of the front cover. The rear cover may be arranged at a side of the main frame opposite to the front cover. In some embodiments, the main frame may include one or more support components to support the radiation source 115, the detector(s) 112, the disinfection device 116, etc. In some embodiments, the gantry 111 may include a housing to protect the main frame and/or the other components (e.g., the radiation source 115, the detector(s) 112, the disinfection device 116, etc.) of the medical device 110. More descriptions regarding the gantry 111 may be found elsewhere in the present disclosure (e.g., FIG. 2 and the descriptions thereof).

In some embodiments, the detector(s) 112 and the radiation source 115 may be oppositely mounted on the gantry 111. In some embodiments, the gantry 111 may rotate and/or move. The detector(s) 112 and the radiation source 115 may rotate along with the rotation of the gantry 111. The table 114 may be configured to locate and/or support a scanned object. A scanned object may be placed on the table 114 and moved into the detecting region 113 (e.g., a space between the detector 112 and the radiation source 115) of the medical device 110. The scanned object may be biological or non-biological. Merely by way of example, the scanned object may include a patient, a man-made object, etc. As another example, the scanned object may include a specific portion, organ, and/or tissue of the patient. In the present disclosure, "subject", "object" or "scanned object" are used interchangeably. In some embodiments, the imaging device 110 may have a relatively long axial field of view (FOV), (e.g., a 2-meter axial FOV in length). Correspondingly, the table 114 may move in a long-distance range (e.g., greater than 2 meters) along the axial direction.

The radiation source 115 may be configured to generate and/or emit radiation rays (e.g., X-rays) to scan the scanned object that is placed on the table 114. The detector 112 may detect the radiation rays (e.g., X rays) penetrated through at least part of the scanned object within the detecting region 113. The detector 112 may generate an electrical signal based on the detected radiation rays. In some embodiments, the detector 112 may include a plurality of detector units, which may be arranged in any suitable manner, for example, a channel direction and a row direction. The detector 112 may include a scintillation detector (e.g., a cesium iodide detector), a gas detector, etc.

The disinfection device(s) 116 may be configured to disinfect one or more spaces and/or one or more components associated with the medical device 110. For example, the disinfection device 116 may disinfect the table 114, the detecting region 113, a space within a threshold distance (e.g., 0.5 m, 1 m, 1.5 m, etc.) of the medical device 110, etc. In some embodiments, the disinfection device(s) 116 may be arranged on a position on the medical device 110. For example, the disinfection device(s) 116 may be arranged on the table 114, the gantry 111 (e.g., the housing of the gantry 111, or in a cavity formed by the housing). More descriptions about the disinfection device 116 may be found elsewhere in the present disclosure (e.g., FIGS. 2 to 15 and the descriptions thereof).

In some embodiments, the medical device 110 may further include an electronic module. The electronic module may be configured to acquire and/or process electrical signals generated by the detector 112. In some embodiments, the electronic module may convert analog signals related to energies of the radiation rays received by the detector 112 into digital signals. The electronic module may determine the imaging data by comparing and/or analyzing the digital signals. In some embodiments, the electronic module may include an adder, a multiplier, a subtractor, an amplifier, a driver circuit, a differential circuit, an integrating circuit, a counter, a filter, an analog-to-digital converter, a lower limit detection circuit, a constant coefficient discriminator circuit, a time-to-digital converter, a coincidence circuit, or the like, or any combination thereof. In some embodiments, if the detector 112 has a relatively long (e.g., 0.75 m to 2 m) axial FOV, the electronic module may have a high data input rate from different detector units. For example, the electronic module may process tens of billions of events per second. In some embodiments, the data input rate may be related to a count of detector units in the detector 112. In some embodiments, the electronic module may be part of the processing device 140.

The network 120 may include any suitable network that can facilitate the exchange of information and/or data for the medical system 100. In some embodiments, one or more components of the medical system 100 (e.g., the medical device 110, the processing device 140, the storage device 150, the terminal device 130) may communicate information and/or data with one or more other components of the medical system 100 via the network 120. For example, the processing device 140 may obtain imaging data from the medical device 110 via the network 120. As another example, the processing device 140 may obtain user instruction(s) from the terminal device 130 via the network 120. The network 120 may be or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the medical system 100 may be connected to the network 120 to exchange data and/or information.

The terminal device 130 may be connected to and/or communicate with the medical device 110 (e.g., the disinfection device 116), the processing device 140, and/or the storage device 150. For example, the terminal device 130 may send a disinfection instruction to the disinfection device 116 to control the disinfection device 116 to perform disinfection. As another example, the terminal device 130 may enable user interactions with the medical system 100. In some embodiments, the terminal device 130 may include a mobile device 131, a tablet computer 132, a laptop computer 133, or the like, or any combination thereof. For example, the mobile device 131 may include a mobile phone, a personal digital assistant (PDA), a gaming device, a navigation device, a point of sale (POS) device, a laptop, a tablet computer, a desktop, or the like, or any combination thereof. In some embodiments, the terminal device 130 may include an input device, an output device, etc. The input device may include alphanumeric and other keys that may be input via a keyboard, a touch screen (for example, with haptics or tactile feedback), a speech input, an eye-tracking input, a brain monitoring system, or any other comparable input mechanism. The input information received through the input device may be transmitted to the processing device 140 via, for example, a bus, for further processing. Other types of input device may include a cursor control device, such as a mouse, a trackball, or cursor direction keys, etc. The output device may include a display, a speaker, a printer, or the like, or a combination thereof. In some embodiments, the terminal device 130 may be part of the processing device 140.

The processing device 140 may process data and/or information obtained from the medical device 110, the terminal device 130, and/or the storage device 150. For example, the processing device 140 may generate an image of a region of interest (ROI, for example, a lung) of an object. The processing device 140 may determine whether the object has an infectious disease based on the image of the object. The processing device 140 may generate a disinfection instruction in response to determining that the object has the infectious disease. The processing device 140 may transmit the disinfection instruction to the disinfection device 116 and the disinfection device 116 may be controlled to perform disinfection according to the disinfection instruction. The processing device 140 may be a central processing unit (CPU), a digital signal processor (DSP), a system on a chip (SoC), a microcontroller unit (MCU), or the like, or any combination thereof. The processing device 140 may be integrated into the high voltage generator.

In some embodiments, the processing device 140 may be a computer, a user console, a single server or a server group, etc. The server group may be centralized or distributed. In some embodiments, the processing device 140 may be local or remote. For example, the processing device 140 may access information and/or data stored in the medical device 110, the terminal device 130, and/or the storage device 150 via the network 120. As another example, the processing device 140 may be directly connected to the medical device 110, the terminal device 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on the medical device 110 and/or the terminal device 130.

The storage device 150 may store data, instructions, and/or any other information. In some embodiments, the storage device 150 may store data obtained from the processing device 140, the terminal device 130, and/or the storage device 150. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the medical system 100 (e.g., the processing device 140, the terminal device 130). One or more components of the medical system 100 may access the data or instructions stored in the storage device 150 via the network 120. In some embodiments, the storage device 150 may be part of the processing device 140.

In some embodiments, the medical system 100 may further include a cooling component. The cooling component may generate, transfer, convey, or conduct a cooling medium, and circulate the cooling medium in the medical device 110 to absorb the heat generated by the medical device 110 during an imaging or treatment process. The cooling component may allow the medical device 110 to maintain a suitable and stable operating temperature (e.g., 25° C., 30° C., 35° C., etc.). In some embodiments, the cooling component may control one or more temperatures of one or more components (e.g., the detector 112, the electronic module, etc.) of the medical device 110. In some embodiments, the cooling medium may be gaseous (e.g., air), liquid (e.g., water), or the like, or any combination thereof. In some embodiments, the cooling component may be completely integrated into the medical device 110 and become a part of the medical device 110. In some embodiments, the cooling component may be partially integrated into the medical device 110 and be associated with the medical device 110.

It should be noted that the above description of the medical system 100 is merely provided for the purposes of illustration, and not intended to limit the scope of the present disclosure. For persons having ordinary skills in the art, multiple variations and modifications may be made under the teachings of the present disclosure.

Figure 2:
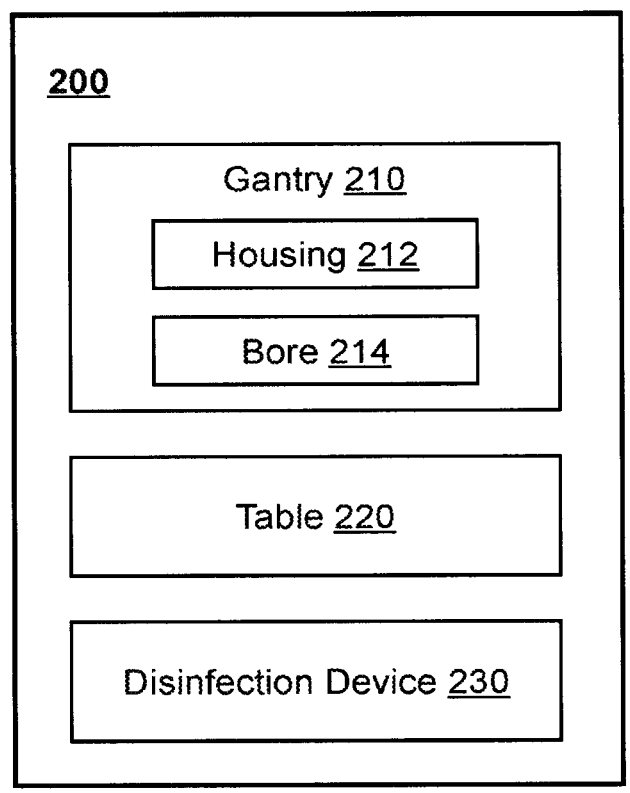
FIG. 2 is a block diagram illustrating an exemplary medical device according to some embodiments of the present disclosure.

FIG. 2 is a block diagram illustrating an exemplary medical device according to some embodiments of the present disclosure. As illustrated in FIG. 2, a medical device 200 may include a gantry 210, a table 220, and one or more disinfection devices 230.

The gantry 210 may include a housing 212 and a bore 214. In some embodiments, the gantry 210 may further include a main frame, a rotating device, one or more support components, or the like, or a combination thereof. The housing 212 may form a cavity around the bore 214 to accommodate one or more components of the medical device 200 (e.g., a radiation source, a detector, the rotating device, the one or more support components, etc.). In some embodiments, the housing 212 may include a front cover and a rear cover as described in FIG. 1. The bore 214 may be configured to accommodate an object for scan. In other words, the bore 214 may include a detecting region (e.g., the detecting region 113) of the medical device 200. In some embodiments, a portion of the housing 212 that forms the bore 214 may also be referred to as a bore wall of the bore 214 or an inner wall of the medical device 200 or the gantry 210. The remaining portion of the housing 212 may also be referred to as an outer wall of the medical device 200 or the gantry 210. The inner wall and the outer wall of the medical device 200 may form the cavity for accommodating one or more components of the medical device 200 (e.g., a radiation source, a detector, the rotating device, the one or more support components, etc.). In some embodiments, a cross-section of the bore 214 may be circular, elliptical, etc.

The table 220 may be configured to support the object and move the object into the bore 214. For example, the table 220 may move along an axial direction of the medical device 200 (e.g., as indicated by the bi-directional arrow illustrated in FIG. 3). In some embodiments, the table 220 may be connected with a table controller configured to control the movement of the table 220. For example, the table controller may control the table 220 to move into the bore 214 after the disinfection device 230 performs disinfection for a preset time period. More descriptions about the table controller may be found elsewhere in the present disclosure (e.g., FIG. 3 and the descriptions thereof).

Each disinfection device 230 may be configured to distinct a space, a component, and/or a subject around the disinfection device 230. For example, the disinfection device 230 may be mechanically arranged on the medical device 200 to disinfect a space associated with the medical device 200. In some embodiments, a disinfection range of the disinfection device 230 may cover the table 220, the bore 214, a space inside the gantry 212 (i.e., the cavity), a space where the medical device 200 is located, etc. In some embodiments, the disinfection range of the disinfection device 230 may be determined based on a position and/or orientation of the disinfection device 230. As used herein, an orientation of a disinfection device refers to a direction in which the disinfection medium is sprayed from the disinfection device. Different positions and/or orientations of the disinfection devices 230 on the medical device 200 may correspond to different disinfection ranges. For example, if the disinfection device 230 is arranged on the inner wall, a disinfection range of the disinfection device 230 may include a space of the bore 214. As another example, if the disinfection device 230 is arranged in the cavity formed by the housing 212 (i.e., between the inner wall and the outer wall of the medical device 200), a disinfection range of the disinfection device 230 may be a space of the cavity. In some embodiments, the disinfection range of the disinfection device 230 may be determined according to a type (also referred to as a disinfection device type) of the disinfection device 230. For example, if the disinfection device 230 is an atomization disinfection device, a disinfection range of the atomization disinfection device on the medical device 200 may be a space (e.g., an examination room) where the medical device 230 is located. As another example, if the disinfection device 230 is an ultraviolet disinfection device, a disinfection range of the ultraviolet disinfection device on the medical device 200 may be a space that can be irradiated by ultraviolet rays. In some embodiments, in order to shorten a disinfection time and improve the disinfection efficiency, two or more disinfection devices 230 may be provided on the medical device 200. For example, the medical device 200 may include two disinfection devices 230 one of which is arranged on the table 220, and the other is arranged on the inner wall. As another example, a single disinfection device 230 may include one or more mutually independent and detachable disinfection modules. The disinfection modules may have different disinfection ranges. The disinfection module may be convenient for users to selectively set according to application scenarios.

In some embodiments, the position and/or orientation of the disinfection device 230 may be changeable to disinfect different spaces around the disinfection device 230. For example, the disinfection device 230 may include a disinfection main portion (e.g., as indicated by the rectangle 1427 in FIG. 14) and a movable portion (e.g., as indicated by the "T" bracket 1430 in FIG. 14). The movable portion may be installed on the medical device 200 (e.g., the table 220, the housing 212, etc.). The disinfection main portion may be connected with the movable portion. The movable portion may move in response to receiving a moving instruction, thereby driving the disinfection main portion to move, rotate, and/or positioning. In such cases, the disinfection range of the disinfection device 230 may be changed accordingly. In some embodiments, the movable portion may include a slide rail, a steering table, a robotic arm, or the like, or any combination thereof. In some embodiments, the disinfection main portion may be detachable for easy replacement.

In some embodiments, the disinfection device 230 may be mechanically arranged on the table 220 for disinfection. For example, when the table 220 is out of the bore 214, the disinfection device 230 may disinfect the table 220 and/or a space around the table 220. As another example, when the table 220 moves into the bore 214, the disinfection device 230 on the table 220 may disinfect the table 220 and/or the bore 214. In some embodiments, the disinfection device 230 may be foldable and/or retractable. For example, when the medical device 200 is being used to scan an object, i.e., the object is lying on the table 220, the disinfection device 230 may be folded or contracted. In such cases, the disinfection device 230 is in a closed or standby state. After the object is scanned, the disinfection device 230 may be unfolded for disinfection, for example, in response to an instruction from a user (e.g., a doctor) via a terminal device. In some embodiments, the disinfection device 230 may include a disinfection main portion and a multiple-section rod comprised by multiple rods and multiple hinge members. A first end of the multiple-section rod may be connected to the disinfection main portion via a hinge member, and a second end of the multiple-section rod may be connected to the medical device 200 so that the disinfection device 230 can be folded or contracted. For example, an upper surface of the table 220 may include a box to accommodate the disinfection device 230. The second end of the multiple-section rod may be connected to the bottom of the box. The disinfection device 230 may be stretched from the box when in use and can be stowed in the box when not in use.

Figure 3:
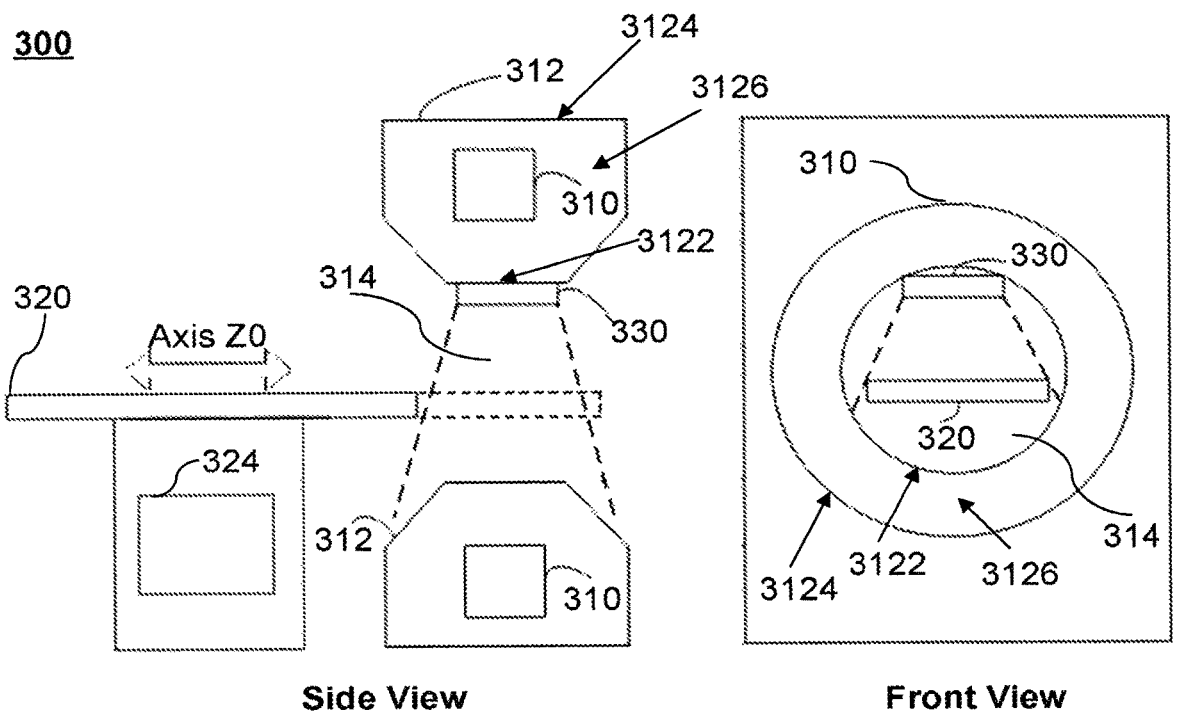
FIG. 3 is a schematic diagram illustrating an exemplary medical device according to some embodiments of the present disclosure.
Figure 4:
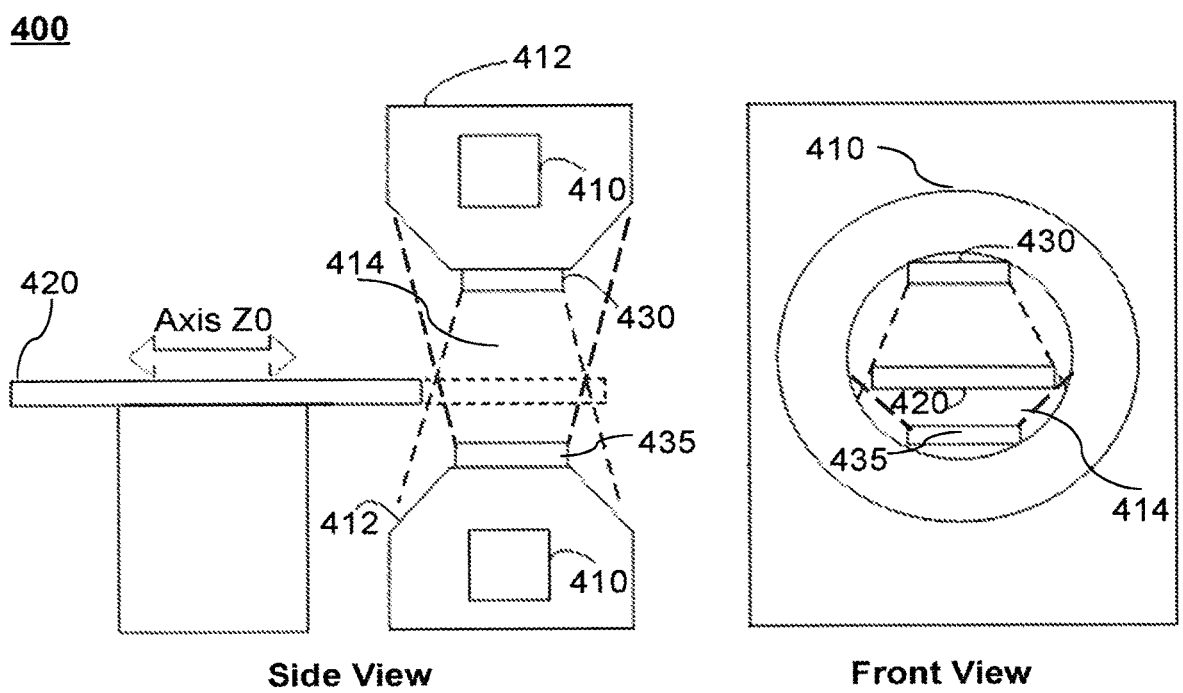
FIG. 4 is a schematic diagram illustrating an exemplary medical device according to some embodiments of the present disclosure.
Figure 5:
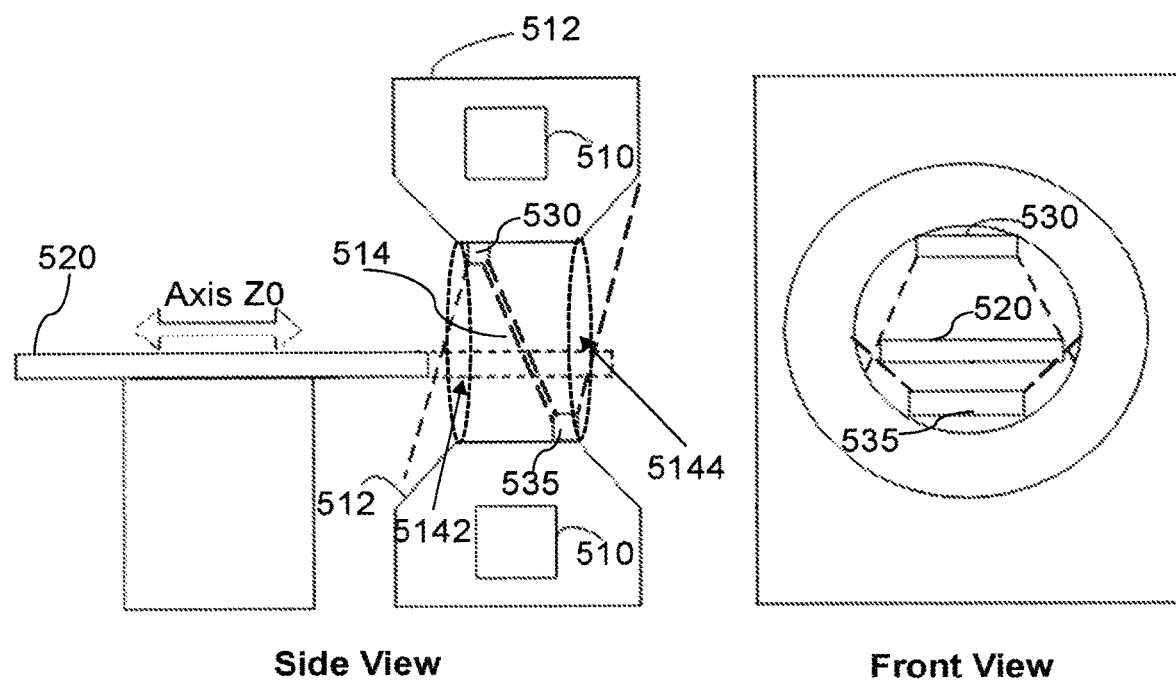
FIG. 5 is a schematic diagram illustrating an exemplary medical device according to some embodiments of the present disclosure.

In some embodiments, the disinfection device 230 may be mechanically arranged on the housing 212. For example, the disinfection device 230 may be mechanically arranged on the inner wall of the medical device 200 to disinfect the bore 214 and/or the table 220 when the table 220 is located in the bore 214 (as shown in FIGS. 3 to 5). As another example, the disinfection device 230 may be mechanically arranged on the outer wall to disinfect the housing 212 and/or a space near the medical device 200 (e.g., a space within a preset range of the medical device 200). In some embodiments, the disinfection device 230 may be arranged at a position of the bore wall facing an upper surface of the table 220 (i.e., a position corresponding to a top end of the bore 214) and/or a position of the bore wall facing a lower surface of the table 220 (i.e., a position corresponding to a bottom end of the bore 214) (as shown in FIG. 4). In such cases, the disinfection device 230 may disinfect the bore 214 and the upper surface and/or the lower surface of the table 220. For brevity, the upper surface of the table 220 refers to a surface of the table 220 that is in contact with the object when the object is scanned. The lower surface of the table 220 refers to a surface of the table 220 opposite to the upper surface of the table 220.

In some embodiments, the bore 214 may include a first opening and a second opening arranged two end portions of the bore 214 along the axis direction of the medical device. The disinfection device 230 may by arranged at an end portion of the housing 212 having the first opening or the second opening. For example, the disinfection device 230 may be arranged on the bore wall corresponding to the first opening or the second opening, so as to disinfect the bore 214 (or the detecting region 113) at a relatively close distance. As another example, the disinfection device 230 may be arranged on the outer wall of the housing 212 near the first opening or the second opening. In some embodiments, the medical device 200 may include two disinfection devices 230 one of which is arranged at a position of the inner wall or outer wall facing the upper surface of the table 212, and the other is arranged at a position of the inner wall or outer wall facing the lower surface of the table 212 (as shown in FIG. 5). In some embodiments, the disinfection ranges of the two disinfection devices may have an overlapped range or not. For example, the disinfection ranges of the two disinfection devices may not overlap to avoid mutual influence. In some embodiments, the disinfection range and/or the orientation of the disinfection device 230 may be adjusted to cover the bore 214 and the table 212 that enters the bore 214.

Figure 6:
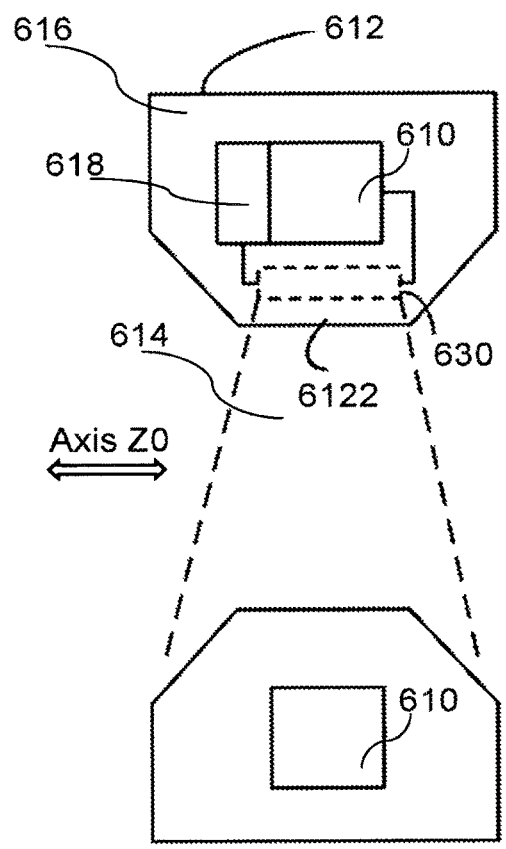
FIG. 6 is a schematic diagram illustrating an exemplary medical device according to some embodiments of the present disclosure.
Figure 6:
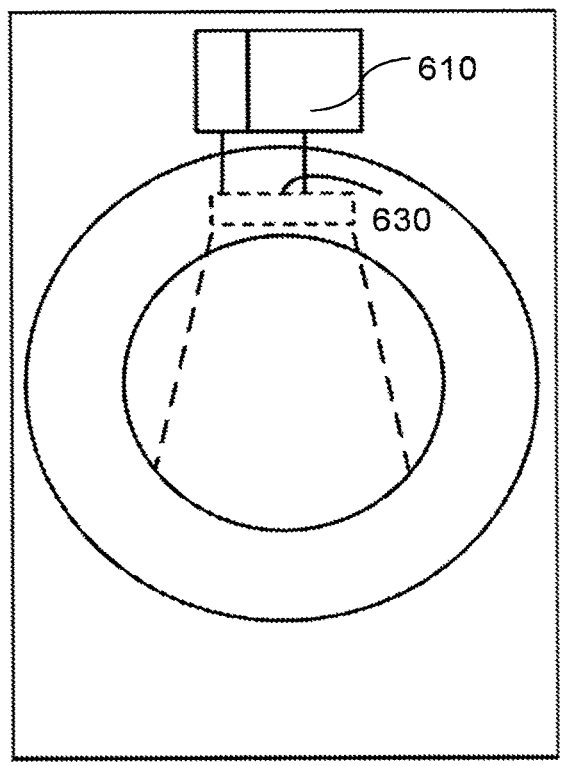
Figure 7A:
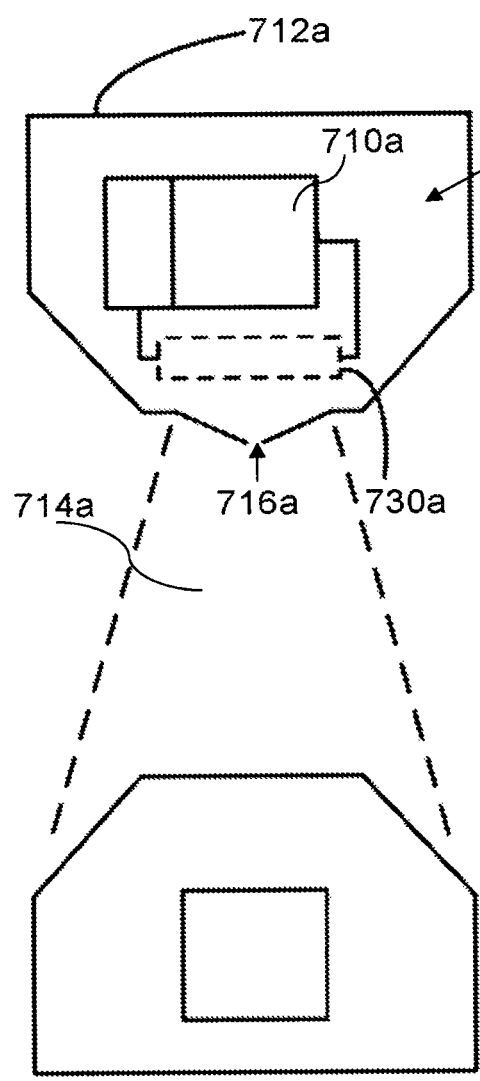
FIG. 7A is a schematic diagram illustrating an exemplary medical device according to some embodiments of the present disclosure.
Figure 7B:
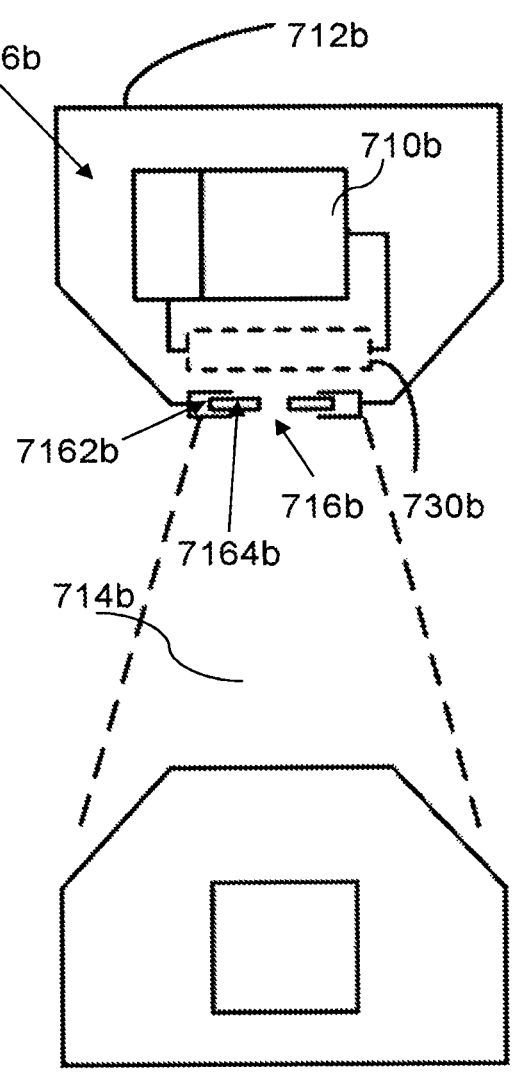
FIG. 7B is a schematic diagram illustrating an exemplary medical device according to some embodiments of the present disclosure.
Figure 8:
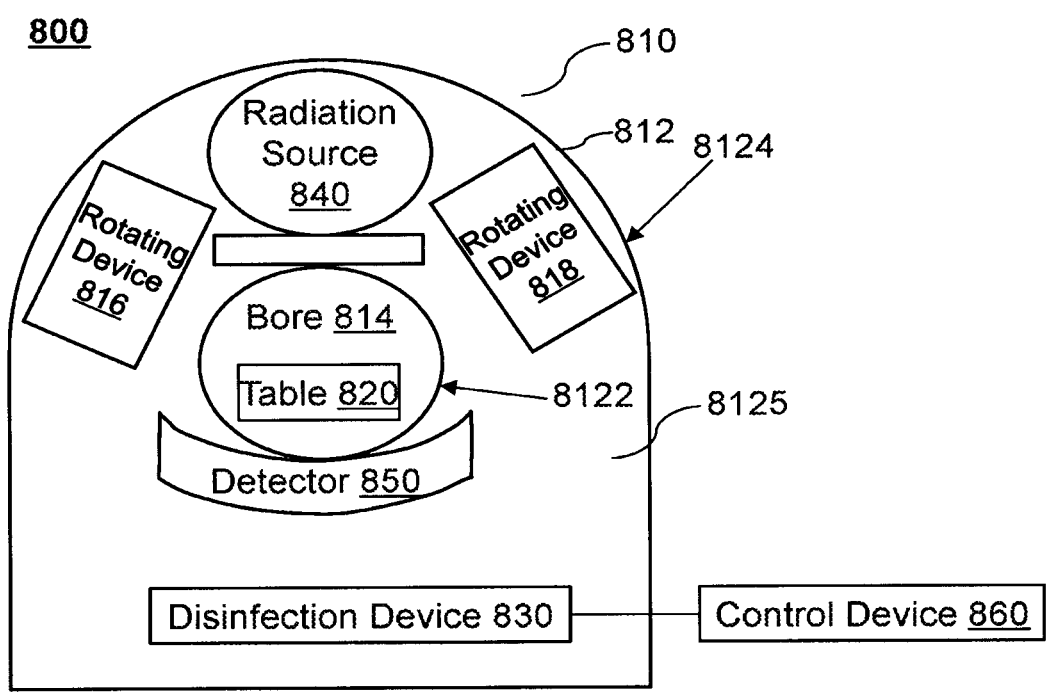
FIG. 8 is a schematic diagram illustrating an exemplary medical device according to some embodiments of the present disclosure.

In some embodiments, the disinfection device 230 may be arranged in the cavity formed by the housing 212. For example, the disinfection device 230 may be arranged on the main frame, the rotating device, and/or the one or more support components in the cavity of the gantry 210 (as shown in FIGS. 6, 7A, and 7B). As another example, the disinfection device 230 may be arranged at any position in the cavity by, for example, a bracket, a base, a connector, or the like (as shown in FIG. 8). The disinfection device 230 may release a disinfection medium during a disinfection process and can disinfect the inside of the gantry 210 of the medical device 200 such as a surface of the cavity, a surface of the one or more components in the cavity, a space of the cavity (also be referred to as a cavity space), etc. In some embodiments, if the disinfection device 230 is arranged on the rotating device, the rotation of the rotating device may drive the disinfection device 230 to rotate, so as to disinfect the cavity through the disinfection medium. If a rotation angle exceeds 360°, the entire cavity can be disinfected without a dead corner. In some embodiments, in order to improve the disinfection effect, two or more disinfection devices 230 may be provided on the rotating device. For example, the medical device 200 may include two disinfection devices 230 one of which is arranged in an upper half portion of the cavity, and the other is arranged in a lower half portion of the cavity.

In some embodiments, the disinfection medium of the disinfection device 230 may penetrate the housing 210 to disinfect a space outside the cavity. For example, the disinfection medium may penetrate the bore wall to the bore 214 to disinfect the bore 214 and/or the table 220 when the table 220 is located in the bore 214 (as shown in FIG. 6). In some embodiments, if the disinfection medium includes radiation energies (e.g., ultraviolet rays, plasma radiation, etc.), at least part of the housing 212 may be made of a material that is permeable to the radiation energies (e.g., ultraviolet rays, plasma radiation, etc.). In this way, while ensuring the sealing and integrity of the housing 212, the disinfection medium may also penetrate the bore wall to disinfect the bore 214. In some embodiments, the at least a part of the housing 212 may be made of glass, quartz glass, polymethyl methacrylate (PMMA), and polycarbonate (PC), or the like, or any combination thereof.

In some embodiments, the housing 212 may be provided with a door to allow the disinfection medium of the disinfection device 230 to pass through when the door is in an open state (as shown in FIGS. 7A and 7B). For example, if the disinfection device 230 is in a standby state, the door on the housing 212 (e.g., the bore wall) may be closed. If the disinfection device 230 is in a working state, the door on the housing 212 may be opened, so that the disinfection medium of the disinfection device 230 (e.g., an atomization disinfection device) may directly pass through the door to disinfect the bore 214. In some embodiments, the door may include a retractable door, a sliding door, or the like, or any combination thereof. The retractable door may include one or more grooves (e.g., a groove 7162b as shown in FIG. 7B)

and one or more door panels. If the door panel(s) extend out the groove(s), the door may be closed; and if the door panel(s) retract into the groove(s), the door may be opened. In some embodiments, if the disinfection device 230 is arranged on the rotating device, the door may be circumferentially arranged on the bore wall. For example, the door may include two annular door panels each of which can be retractable. In some embodiments, a rotating speed of the rotating device may be matched with a moving speed of the table 220.

In some embodiments, the medical device 200 may further include an air inlet and an air outlet arranged on the housing 212. The disinfection device 230 may be arranged at the air inlet and/or the air outlet. More descriptions regarding the disinfection device being arranged at the air inlet and/or the air outlet may be found elsewhere in the present disclosure (e.g., FIGS. 9 to 13 and the descriptions thereof).

In some embodiments, the disinfection device 230 may include an ultraviolet disinfection device, a plasma disinfection device, an atomization disinfection device, an ozone disinfection device, a photocatalyst disinfection device, or the like, or any combination thereof.

The ultraviolet disinfection device may utilize ultraviolet rays of appropriate wavelength to destroy a molecular structure of deoxyribonucleic acid (DNA) or ribonucleic acid (RNA) in microbial cells to kill the microbial cells, thereby achieving an effect of sterilization and disinfection. Exemplary the ultraviolet disinfection devices may include a UVA germicidal lamp, a UVC germicidal lamp, etc.

The plasma disinfection device may utilize plasma to kill living microorganisms. For example, a chemically active, cold atmospheric plasma may trigger a plurality of physical and chemical processes. Organic molecules (e.g., DNA, RNA, protein, etc.) of the living microorganisms may be bombarded or oxidized by electrons, ions, and/or short-lived neutral chemical species to decompose, thereby achieving the effect of sterilization and disinfection. In some embodiments, the plasma disinfection device may utilize a bipolar plasma electrostatic field to decompose and/or destroy negatively changed microorganisms. In some embodiments, the plasma disinfection device may further polarize and adsorb (or filter) the dust, and then use components such as a drug-impregnated activated carbon component, an electrostatic net, or a photocatalyst catalysis device, etc., for secondary sterilization and filtration. Finally, a controlled environment may be kept at a standard of "sterile clean room" by quickly circulating a large amount of treated clean air.

The atomization disinfection device may atomize a disinfectant liquid and spray the disinfectant liquid into a space to be disinfected to achieve the purpose of disinfection. In some embodiments, after a suspension time of the atomized disinfection liquid in the space is greater than a threshold time period (e.g., 2 hours, 3 hours, 4 hours, etc.), almost all microorganisms (e.g., bacteria) in the space may be killed. In some embodiments, the atomization disinfection device may atomize a disinfectant liquid using an ultrasonic atomization technique, a pressure atomization technique, a gas atomization technique, or the like, or any combination thereof. In some embodiments, the ultrasonic atomization technique may adopt an electronic over-frequency oscillation technique (e.g., an adopted oscillation frequency is 1.7 MHz, which is beyond an audible range of humans and is not harmful to humans or animals), in which the disinfectant liquid may be thrown away from the liquid surface to produce a natural mist according to the high-frequency resonance of an atomizer. In some embodiments, the disinfectant liquid may be atomized into fine mist particles with a diameter of 1 to 10 μm.

The photocatalyst disinfection device may include an activation medium for disinfection under a light. For example, for a titanium dioxide photocatalyst disinfection device (i.e., the activation medium is titanium dioxide particles), when the titanium dioxide particles are irradiated with ultraviolet rays with a wavelength of 388 nm or less, due to the absorption of light energy, the inside of the particles may be excited to produce electron-hole pairs (i.e., photo-generated carriers). Then the electron-hole pairs may quickly migrate to the surface of the particles and activate the oxygen and moisture adsorbed by the particles to produce active free hydroxyl groups (—OH) and active oxygen (—O). When toxic and harmful substances (e.g., pollutants, bacteria, etc.) are adsorbed on the surface of the particles, the toxic and harmful substances may undergo a chain degradation reaction, thereby degrading the toxic and harmful substances in the air. In some embodiments, the toxic and harmful substances may include formaldehyde, mites, etc.

In some embodiments, the disinfection device 230 may be connected with a control device of the medical device 200 (as shown in FIG. 8). The control device may send a control instruction to the disinfection device 230 to control the disinfection device 230. In some embodiments, the control instruction may include a turning on instruction, a turning off instruction, a disinfection instruction, a scheduled disinfection instruction, a disinfection intensity control instruction, or the like, or any combination thereof. As used herein, the disinfection instruction refers to an instruction for controlling the disinfection device 230 to perform disinfection. The scheduled disinfection instruction refers to an instruction for controlling the disinfection device 230 to perform disinfection within a predetermined time period. In some embodiments, the control instruction may include one or more parameters associated with the disinfection device 230. For example, the one or more parameters may include a disinfection intensity, a disinfection duration, a concentration of the disinfection medium of the disinfection device 230, etc. In some embodiments, the control instruction may be generated before the medical device 200 scans the object. For example, when the medical device 200 starts to scan the object, a scheduled disinfection instruction may be generated in time to control the disinfection device 230 to perform disinfection after the scan is completed. In some embodiments, the medical device 200 may further include an acquisition module configured to acquire information associated with the medical device and/or the object. The control instruction may be generated based on the information associated with the medical device and/or the object. For example, the acquisition module may be connected with a monitoring device. A scheduled disinfection instruction may be generated in response to identifying that the information associated with the medical device and/or the object indicating that the object is about to be scanned. More descriptions regarding the control device may be found elsewhere in the present disclosure (e.g., FIG. 15 and the descriptions thereof). In some embodiments, the acquisition module may be integrated into the control device.

In some embodiments, the acquisition module may be connected with a monitoring device, a temperature measurement device, a medical database, an image processing device, etc., to acquire information associated with the medical device and/or the object. The control device may further configured to determine whether the medical device 200 needs to be disinfected based on the information associated with the medical device and/or the object and generate a control instruction in response to determining that the medical device needs to be disinfected. In some embodiments, the control device may determine that the medical device needs to be disinfected when the information associated with the at least one of the medical device or the object satisfies a compliance condition. More descriptions regarding the acquisition module and the control device may be found elsewhere in the present disclosure (e.g., FIGS. 16 to 19 and the descriptions thereof).

In some embodiments, the medical device 200 may be arranged in a medical cabin of a medical system. The medical system may include an air purification device. More descriptions regarding the air purification device may be found elsewhere in the present disclosure (e.g., FIGS. 20 to 23, 24A and 24B and the descriptions thereof).

According to some embodiments of the present disclosure, since the medical device 200 is directly used for patients, the medical device 200 is easily contaminated by viruses and bacteria from the patients. The medical device 200 disclosed in the present disclosure can be disinfected by the disinfection device(s) 230 provided on the medical device 200, which is convenient and fast, and there is no need to wait for a disinfection staff to bring a disinfection device from other places, thereby saving disinfection manpower consumption, shortening the disinfection time, and improving the disinfection efficiency.

It should be noted that the above description of the medical device 200 is merely provided for the purposes of illustration, and not intended to limit the scope of the present disclosure. For persons having ordinary skills in the art, multiple variations and modifications may be made under the teachings of the present disclosure. In some embodiments, the disinfection device 230 may be configured according to actual needs. For example, one or more ultraviolet disinfection devices may be arranged around a region or space to be disinfected. In some embodiments, a count of the ultraviolet disinfection devices may be increased. As another example, a spray port of an atomization disinfection device may be adjusted based on a position of a region or space to be disinfected. As a further example, an ionization density of plasma of a plasma disinfection device may be adjusted according to actual needs.

FIG. 3 is a schematic diagram illustrating an exemplary medical device according to some embodiments of the present disclosure. As illustrated in FIG. 3, a left portion in FIG. 3 may present a side view of a medical device 300, and a right portion in FIG. 3 may present a front view of the medical device 300. The side view may be parallel to an axis of the medical device 300 denoted by Z0; the front view may be perpendicular to the axis Z0 (also referred to as an axial direction Z0) of the medical device 300. The medical device 300 may be the same as or similar to the medical device 200 as described in FIG. 2. For example, the medical device 300 may include a gantry 310, a table 320, and a disinfection device 330. The gantry 310 may include a housing 312 and a bore 314. The housing 312 may include an inner wall 3122 and an outer wall 3124 which forms a cavity 3126 around the bore 314 to accommodate one or more components of the medical device 300 (e.g., a radiation source, a detector, the rotating device, the one or more support components, etc.). More descriptions for components of the medical device 300 may be found elsewhere in the present disclosure (e.g., FIG. 2 and the descriptions thereof).

The disinfection device 330 may be arranged on a position of a bore wall of the bore 314 (i.e., the inner wall 3122 of the gantry 310). For example, the disinfection device 330 may be arranged on a top position of the inner wall 1322 facing the upper surface of the table 320. A disinfection range of the disinfection device 330 may cover the bore 314 (as indicated by the dotted lines illustrated in FIG. 3). In other words, the disinfection device 330 may disinfect the bore 314 and/or at least portion of the table 320 that is located in the bore 314.

The medical device 300 may further include a table controller 324 configured to control a movement of the table 320. In some embodiments, the table controller 324 may control the table 320 to move into the bore 314 after the disinfection device 330 performs disinfection for a preset time period. For example, the disinfection device 330 may disinfect the bore 314 for the preset time period, then the table 320 may be moved into the bore 314 to be disinfected by the disinfection device 330. During the movement of the table 320, the disinfection device 330 may continuously disinfect the portion of the table 320 located in the bore 314. That is, a portion of the table 320 that enters the bore 314 early may have a longer disinfection time than a portion of the table 320 that enters the bore 314 later. As another example, after the disinfection device 330 is controlled to disinfect the bore 314 for the preset time period, the disinfection device 330 may be temporarily turned off. Then, the table 320 may be controlled to move into the bore 314 until the table 320 moves to a maximum stroke of the table 320. In response to a determination that the table 320 reaches the maximum stroke, the disinfection device 330 may be controlled (e.g., by a control device illustrated in FIG. 15) to turn on. That is, each portion of the table 320 located in the bore 314 may have a same disinfection time. In some embodiments, the disinfection device 330 may be controlled to be turned on in response to the disinfection range of the disinfection device 330 that covers the table 320 to be the maximum. In some embodiments, the preset time period may be set according to a default setting of the medical device 300 or preset by a user or operator via the terminal device 130. In some embodiments, the preset time period may be determined according to practical needs, for example, 5 seconds, 10 seconds, 15 seconds, 20 seconds, 30 seconds, 45 seconds, 60 seconds, etc.

Figure 15:
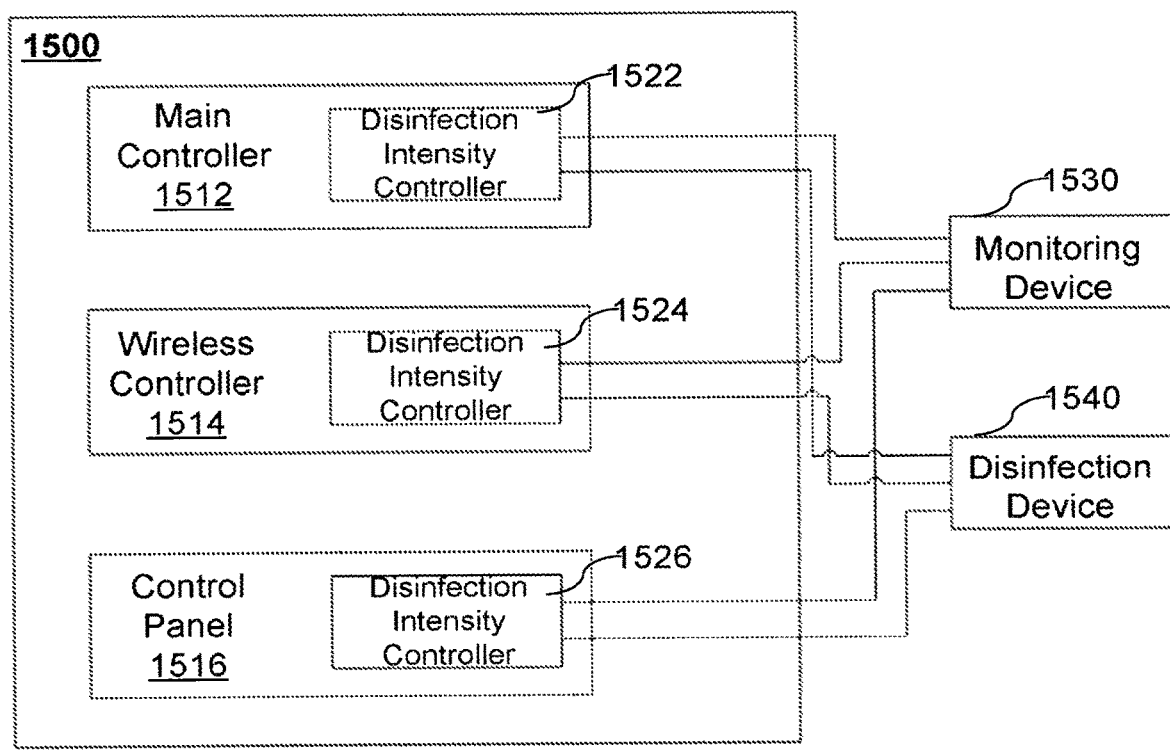
FIG. 15 is a schematic diagram illustrating an exemplary control device of a disinfection device according to some embodiments of the present disclosure.

In some embodiments, the table controller 324 may be integrated into the control device as described in FIG. 8 and/or FIG. 15.

FIG. 4 is a schematic diagram illustrating an exemplary medical device according to some embodiments of the present disclosure. As illustrated in FIG. 4, a left portion in FIG. 4 may present a side view of a medical device 400, and a right portion in FIG. 4 may present a front view of the medical device 400. The side view may be parallel to an axis of the medical device 400 denoted by Z0; the front view may be perpendicular to the axis Z0 (also referred to as an axial direction Z0) of the medical device 400. The medical device 400 may be the same as or similar to the medical device 300 as described in FIG. 3. For example, the medical device 400 may include a gantry 410, a table 420, and a disinfection device 430. The gantry 410 may include a housing 412 and a bore 414. More descriptions for components of the medical device 400 may be found elsewhere in the present disclosure (e.g., FIG. 2 or FIG. 3 and the descriptions thereof).

In some embodiments, the disinfection device 430 may also be referred to as a first disinfection device. The first disinfection device 430 may be arranged on a top position of a bore wall of the bore 414. The medical device 400 may further include a second disinfection device 435 arranged on a bottom position of the bore wall of the bore 414. Both disinfection ranges (as indicated by the dotted lines illustrated in FIG. 4) of the first disinfection device 430 and the second disinfection device 435 may cover the bore 414. With the arrangement shown in FIG. 4, both the upper surface and the lower surface of the table 420 may be disinfected.

FIG. 5 is a schematic diagram illustrating an exemplary medical device according to some embodiments of the present disclosure. As illustrated in FIG. 5, a left portion in FIG. 5 may present a side view of a medical device 500, and a right portion in FIG. 5 may present a front view of the medical device 500. The side view may be parallel to an axis of the medical device 500 denoted by Z0; the front view may be perpendicular to the axis Z0 (also referred to as an axial direction Z0) of the medical device 500. The medical device 500 may be the same as or similar to the medical device 400 as described in FIG. 3. For example, the medical device 500 may include a gantry 510, a table 520, and a disinfection device 530. The gantry 510 may include a housing 512 and a bore 514. More descriptions for components of the medical device 500 may be found elsewhere in the present disclosure (e.g., FIG. 2 or FIG. 3 and the descriptions thereof).

The bore 514 may include a first opening 5142 and a second opening 5144 (as indicated by dotted ellipses illustrated in FIG. 5). The disinfection device 530 (also be referred to as a first disinfection device) may be arranged at an end portion of the housing 512 (or a bore wall of the bore 414) having the first opening 5142 or the second opening 5144. In some embodiments, the medical device 500 may further include a second disinfection device 535. The first disinfection device 530 and the second disinfection device 535 may be arranged on different positions of the bore wall of the bore 514. For example, the first disinfection device 530 may be arranged on a top position of the bore wall of the bore 514 and the second disinfection device 535 may be arranged on a bottom position of the bore wall of the bore 514 In some embodiments, the disinfection ranges (as indicated by the dotted lines illustrated in FIG. 5) of the first disinfection device 530 and the second disinfection device 535 may overlap or not.

FIG. 6 is a schematic diagram illustrating an exemplary medical device according to some embodiments of the present disclosure. As illustrated in FIG. 6, a left portion in FIG. 6 may present a side view of a medical device 600, and a right portion in FIG. 6 may present a front view of the medical device 600. The side view may be parallel to an axis of the medical device 600 denoted by Z0; the front view may be perpendicular to the axis Z0 (also referred to as an axial direction Z0) of the medical device 600. The medical device 600 may be the same as or similar to the medical device 300 as described in FIG. 3. For example, the medical device 600 may include a gantry 610, a table (not shown), and a disinfection device 530. The gantry 610 may include a housing 612 and a bore 614. More descriptions for components of the medical device 600 may be found elsewhere in the present disclosure (e.g., FIG. 2 or FIG. 3 and the descriptions thereof).

The gantry 610 may include one or more components 618 such as a rotating device, one or more support components, a radiation source, etc. The housing 612 may form a cavity 616 configured to accommodate the one or more components 618 of the gantry 610. The cavity 616 may also accommodate other components (e.g., a radiation source, a detector, etc.) of the medical device 600. The disinfection device 620 may be arranged on the one or more components 618 to disinfect the cavity 616.

In some embodiments, a disinfection medium of the disinfection device 630 may penetrate at least part of a bore wall 6122 of the bore 614 to disinfect the bore 614 and/or the table when the table is located in the bore 614. In some embodiments, if the disinfection medium includes radiation energies (e.g., ultraviolet rays, plasma radiation, etc.), the at least part of the bore wall 6122 may be made of a material that is permeable to the disinfection medium. In some embodiments, the material that is permeable to the disinfection medium may include glass, quartz glass, polymethyl methacrylate (PMMA), and polycarbonate (PC), or the like, or any combination thereof.

In some embodiments, the medical device 600 may be provided with two or more disinfection devices arranged on different portions in the cavity 616. For example, the medical device 600 may include a first disinfection device and a second disinfection device located two sides of the bore 614 in the cavity 616. For example, one of the first disinfection device and the second disinfection device is arranged above the bore 614 in the cavity 616, and the other is arranged below the bore 614 in the cavity 616.

FIG. 7A is a schematic diagram illustrating an exemplary medical device according to some embodiments of the present disclosure. As illustrated in FIG. 7A, a medical device 700A may be the same as or similar to the medical device 600 as described in FIG. 6. For example, the medical device 700A may include a gantry 710a and a disinfection device 730a. The gantry 710a may include a housing 712a and a bore 714a. The housing 712a may include a cavity 7126a where the disinfection device 730a is located. More descriptions for components of the medical device 700 may be found elsewhere in the present disclosure (e.g., FIG. 2, FIG. 3, or FIG. 6, and the descriptions thereof).

The housing 712a may be provided with a door 716a to allow a disinfection medium of the disinfection device 730a to pass through when the door 716a is in an open state, such that the disinfection medium of the disinfection device 730a may transmit from the cavity 7126a to the bore 714a. In some embodiment, if the disinfection device 230 is in a standby state or the medical device 700A is scanning, the door 716a may be closed. If the disinfection device 730a is in a working state, the door 716a may be opened, so that the disinfection medium of the disinfection device 730a (e.g., an atomization disinfection device, an ultraviolet disinfection device, etc.) may directly pass through the door 716a to disinfect the bore 714a.

FIG. 7B is a schematic diagram illustrating an exemplary medical device according to some embodiments of the present disclosure. As illustrated in FIG. 7B, a medical device 700B may be the same as or similar to the medical device 700A as described in FIG. 7A. For example, the medical device 700B may include a gantry 710b and a disinfection device 730b. The gantry 710b may include a housing 712b and a bore 714b. The housing 712b may include a cavity 7126b where the disinfection device 730b is located. The housing 712b may be provided with a door 716b to allow a disinfection medium of the disinfection device 730b to pass through when the door 716b is in an open state, such that the disinfection medium of the disinfection device 730b may transmit from the cavity 7126b to the bore 714b.

The door 716b may be a retractable door. The door 716b may include at least one groove 7162b and at least one door plate 7164b. When the door plate 7164b protrudes from the groove 7162b, the door 716b may be in a closed state. Conversely, when the door plate 7164b is retracted into the groove 7162b, the door 716b may be in an open state.

FIG. 8 is a schematic diagram illustrating an exemplary medical device according to some embodiments of the present disclosure. FIG. 8 illustrates a front view of the medical device 800. The front view may be perpendicular to an axial direction (or a direction in which a table 820 moves) of the medical device 800. The medical device 800 may be the same as or similar to the medical device 200 as described in FIG. 2. For example, the medical device 800 may include a gantry 810, a table 820, and a disinfection device 830. The gantry 810 may include a housing 812 and a bore 814. The housing 812 may include an inner wall 8122 and an outer wall 8124 which forms a cavity 8125 around the bore 814 to accommodate one or more components of the medical device 800 (e.g., one or more support components, etc.). More descriptions for components of the medical device 800 may be found elsewhere in the present disclosure (e.g., FIG. 2 and the descriptions thereof).

The medical device 800 may further include a radiation source 840 and a detector 850. The radiation source 840 and the detector 850 may be mounted on the gantry 810. For example, the gantry 810 may include one or more rotating devices (e.g., a first rotating device 816 and a second rotating device 818) arranged in the cavity 8125 formed by the housing 812. The radiation source 840 (e.g., a tube) and the detector 850 may be mounted on the one or more rotating devices. In some embodiments, each rotating device may include a fixed body, and a rotor that is rotatably mounted on the fixed body via a support component. The fixed body may be mounted on a main frame of the gantry 810. The disinfection device 830 may be arranged at any position in the cavity 8125 to disinfect the cavity 8125. For example, the disinfection device 830 may be arranged on a position of an inner wall 8122 of the housing 812. As another example, the disinfection device 830 may be arranged in the cavity 8125 via a support component (e.g., a bracket) to position the disinfection device 830 at a desired position.

In some embodiments, the medical device 800 may adopt a heat dissipation technique including a water-cooling technique, an air-cooling technique, or the like, or a combination thereof. Generally, if the medical device 800 adopts the air-cooling technique, bacteria, viruses etc., may easily enter the cavity of the medical device through the airflow, and then spread into the space of the cavity 8125, thereby forming a source of infection. According to some embodiments of the present disclosure, the disinfection device 830 of the medical device 800 may disinfect the cavity 8125. Thus, even if the bacteria and viruses enter the cavity 8125 of the medical device 800 through the airflow, the inside of the medical device 800 can be disinfected to prevent the bacteria and viruses from spreading into the cavity 8125 and forming a source of infection. In some embodiments, the internal disinfection of the cavity 8125 cooperates with the external disinfection (i.e., the disinfection outside the cavity 8125, such as the disinfection of the table 820) of the medical device 800, a medical examination room where the medical device 800 is located can be disinfected quickly, timely, and comprehensively without hindering the normal scanning of the medical device 800.

In some embodiments, the medical device 800 may further include a control device 860 configured to control the disinfection device 830. For example, the control device 860 may control the disinfection device 830 to be turned on or off. More descriptions about the control device may be found elsewhere in the present disclosure (e.g., FIG. 15 and the description thereof).

Figure 9:
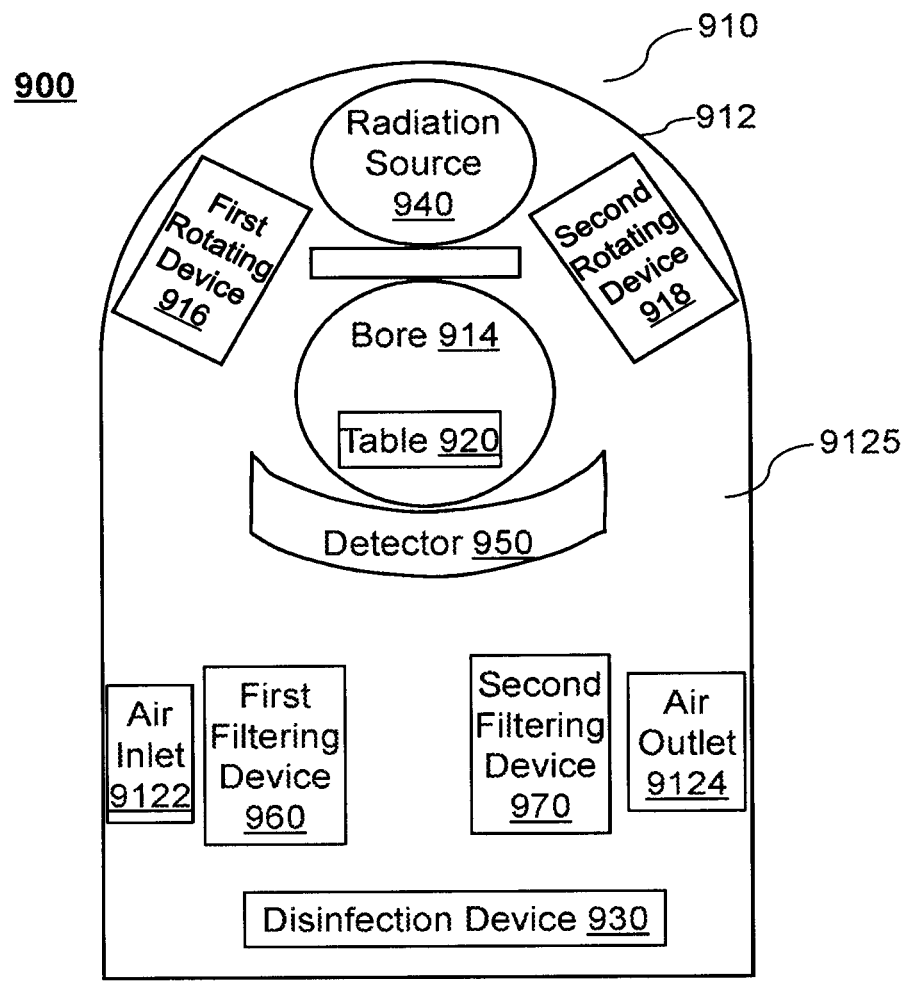
FIG. 9 is a schematic diagram illustrating an exemplary medical device according to some embodiments of the present disclosure.

FIG. 9 is a schematic diagram illustrating an exemplary medical device according to some embodiments of the present disclosure. FIG. 9 illustrates a front view of the medical device 900. The front view may be perpendicular to an axial direction (or a direction in which a table 920 moves) of the medical device 900. The medical device 900 may be the same as or similar to the medical device 800 as described in FIG. 8. For example, the medical device 900 may include a gantry 910, a table 920, a disinfection device 930, a radiation source 940, and a detector 950. The gantry 910 may include a housing 912, a bore 914, a first rotating device 916, and a second rotating device 918. The housing 912 of the gantry 910 may form a cavity 9125 configured to accommodate one or more components (e.g., the radiation source 940, the detector 950) of the medical device 900. More descriptions for components of the medical device 900 may be found elsewhere in the present disclosure (e.g., FIG. 2 or FIG. 8 and the descriptions thereof).

The medical device 900 may further include an air inlet 9122 and an air outlet 9124 arranged on the housing 912. In some embodiments, the air inlet 9122 and the air outlet 9124 may be provided on opposite walls of the housing 912. In some embodiments, the air inlet 9122 and/or the air outlet 9124 may be provided with one or more filtering devices (e.g., a first filtering device 960, a second filtering device 970) in the cavity 9125. Each filtering device may be configured to filter the air passing through the filtering device to filter out at least part of particles, bacteria, and/or viruses. For example, the first filtering device 960 provided at the air inlet 9122 may filter the air entering the cavity 9125 through the air inlet 9122. As another example, the second filtering device 970 provided at the air outlet 9124 may filter the air discharged from the cavity 9125 through the air outlet 9124. In some embodiments, in order to improve the filtering effect of the filtering device, an effective filtering area of the filtering device may be appropriately increased, such as by adopting a folded filter net, designing the filtering device with an internal air duct.

Figure 10:
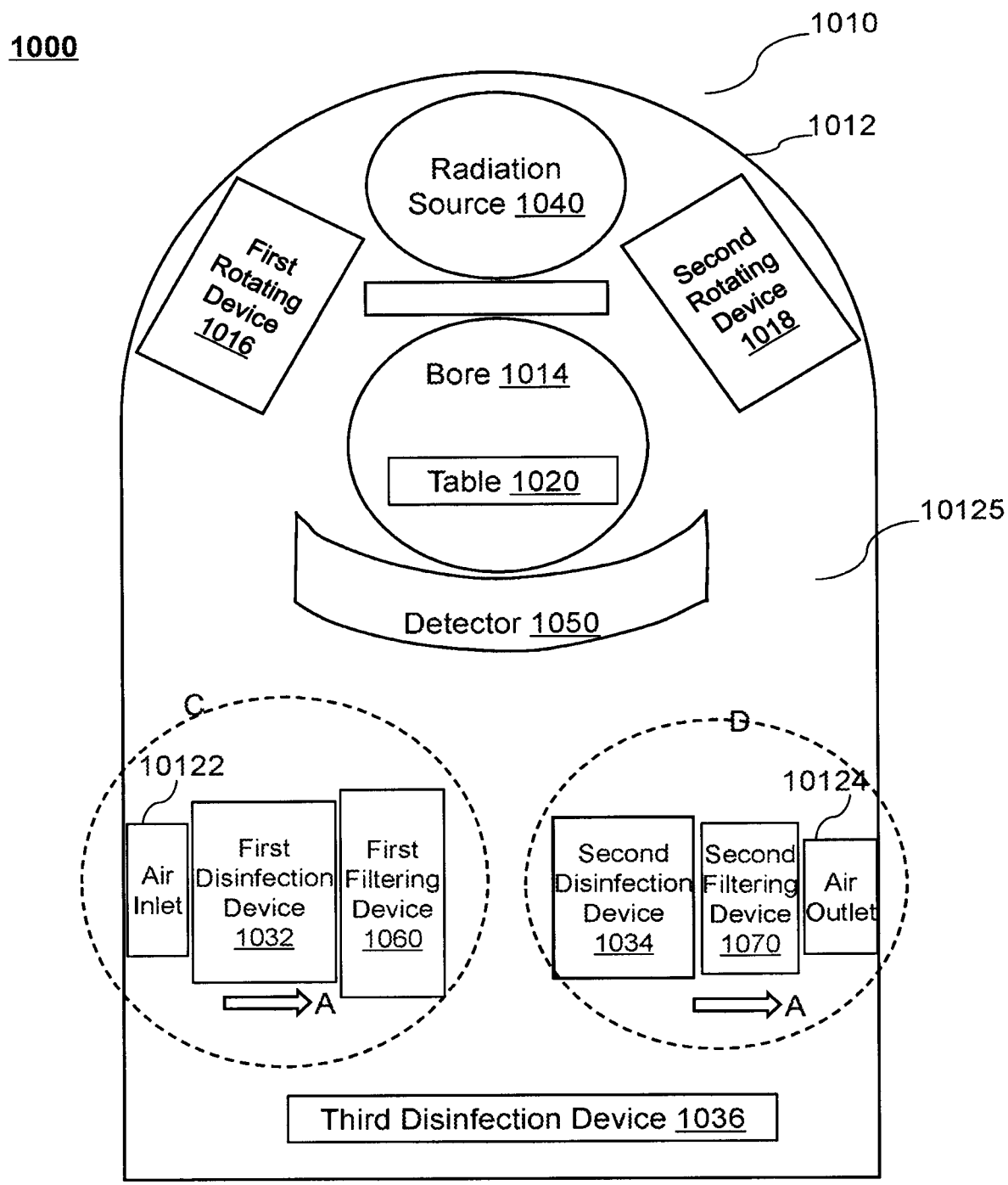
FIG. 10 is a schematic diagram illustrating an exemplary medical device according to some embodiments of the present disclosure.
Figure 11:
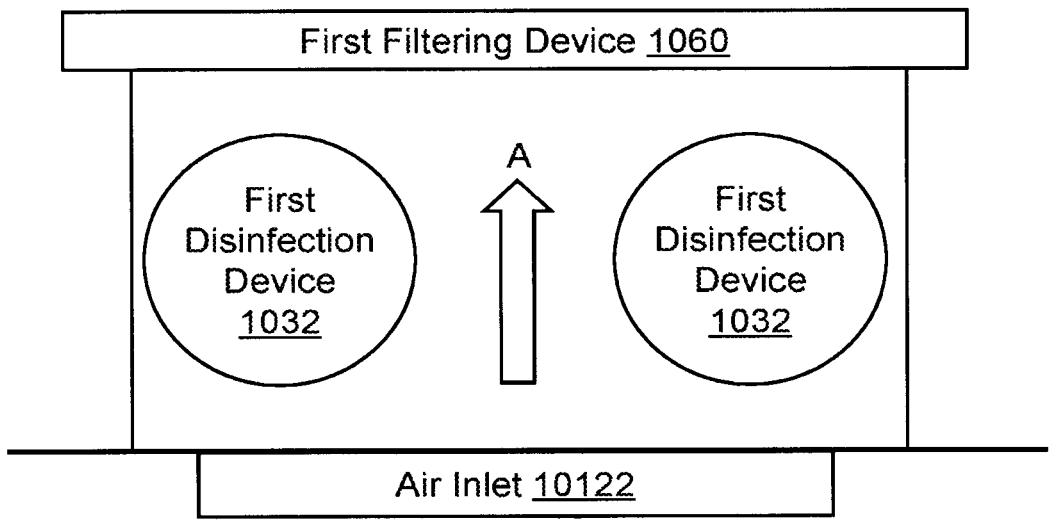
FIG. 11 is an enlarged view of part C in FIG. 10.
Figure 12:
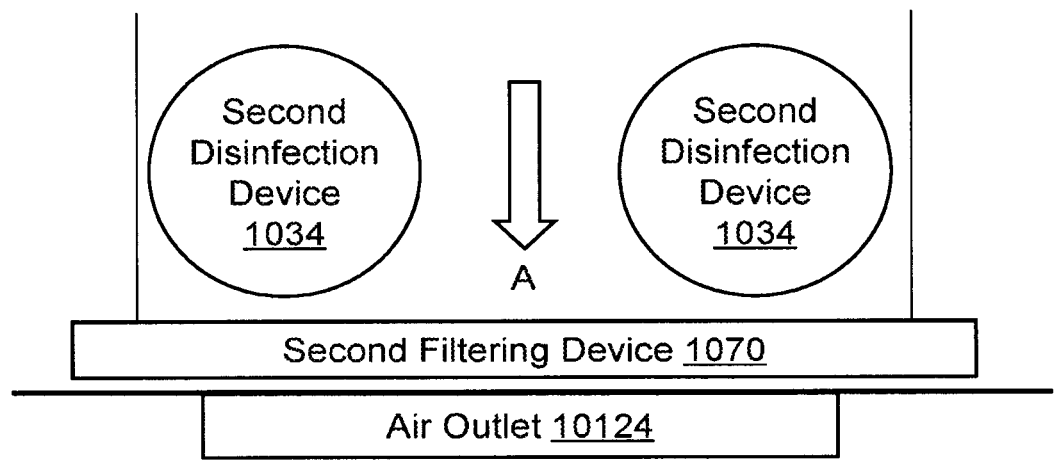
FIG. 12 is an enlarged view of part D in FIG. 10.

In some embodiments, the disinfection device 930 may be arranged around the air inlet 9122 and/or the air outlet 9124 to disinfect air flows in or out of the cavity 9125. For example, the disinfection device 930 may be arranged between the air inlet 9122 and the first filtering device 960 (as shown in FIG. 10 or FIG. 11). As another example, the second filtering device 970 may be arranged between the air outlet 9124 and the disinfection device 930 (as shown in FIG. 10 or FIG. 12).

In some embodiments, the one or more filtering devices may include a high-efficiency particulate air (HEPA) filter, an activated carbon filter, a photocatalyst filter, an electrostatic adsorption filter, or the like, or any combination thereof. The HEPA filter may allow air to pass through but prevent fine particles from passing through. The HEPA filter may be a relatively efficient filter for pollutants such as smoke, dust, or bacteria. For example, the HEPA filter may filter more than 99.7% of particles with a diameter smaller than 0.3 μm (approximately equal to $\frac{1}{200}$ of a diameter of a hair). The activated carbon filter may have good adsorption. Main factors affecting the adsorption of activated carbon may depend on a development degree of structures of pores (e.g., a count or a size of pores) inside the activated carbon. The activated carbon with a large number of pores slightly larger than a diameter of a bacterium/virus may have a relatively strong adsorption capacity. The photocatalyst filter may be made by lattice doping nano-level powders with a variety of nano-level light-sensitive semiconductor media to ensure air permeability and sufficient contact and then mixing and processing with a carrier. In some embodiments, the photocatalyst filter may effectively remove harmful gases and peculiar smells in the air such as carbon monoxide, nitrogen oxides, hydrocarbons, aldehydes, benzene etc., and decompose the above mentioned harmful gases and peculiar smells into harmless carbon dioxide and water. In some embodiments, the photocatalyst filter may also have a sterilizing effect on, for example, *Escherichia coli, Staphylococcus aureus*, etc., so as to decompose compounds released from dead bacteria while sterilizing. It should be noted that the photocatalyst filter may only need to be exposed to light (e.g., ultraviolet light), its catalytic ability can be restored. An activation medium of the photocatalyst filter may be not consumed and can be regenerated for long-term use. The electrostatic adsorption filter may adopt the principle of electrostatic adsorption to adsorb microorganisms (e.g., bacteria, viruses, etc.) on the electrostatic adsorption filter to prevent the microorganisms from passing through the electrostatic adsorption filter.

In some embodiments, the one or more filtering devices and one or more disinfection devices may be integrated into an air purification device. More descriptions regarding the air purification device may be found elsewhere in the present disclosure (e.g., FIGS. 20 to 23, and the descriptions thereof).

FIG. 10 is a schematic diagram illustrating an exemplary medical device according to some embodiments of the present disclosure. FIG. 10 illustrates a front view of the medical device 1000. The front view may be perpendicular to an axial direction (or a direction in which a table 1020 moves) of the medical device 1000. The medical device 1000 may be the same as or similar to the medical device 900 as described in FIG. 9. For example, the medical device 1000 may include a gantry 1010, a table 1020, one or more disinfection devices (including a first disinfection device 1032, a second disinfection device 1034, and a third disinfection device 1036), a radiation source 1040, a detector 1050, and one or more filtering devices (including a first filtering device 1060 and a second filtering device 1070). The gantry 1010 may include a housing 1012, a bore 1014, a first rotating device 1016, and a second rotating device 1018. As another example, the housing 1012 of the gantry 1010 may form a cavity 10125 configured to accommodate one or more components (e.g., the radiation source 1040, the detector 1050) of the medical device 1000. The medical device 1000 may further include an air inlet 10122 and an air outlet 10124 arranged on the housing 1012. More descriptions for components of the medical device 1000 may be found elsewhere in the present disclosure (e.g., FIG. 2 or FIG. 9 and the descriptions thereof).

The first disinfection device 1032 may be arranged between the air inlet 10122 and the first filtering device 1060. The second filtering device 1070 may be arranged between the air outlet 10124 and the second disinfection device 1034. In some embodiments, the third disinfection device 1036 may be arranged in others positions (e.g., on the first rotating device 1016) in the cavity 10125. It should be noted that a position of the air inlet 10122 and/or the air outlet 10124 may not be limited.

FIG. 11 is an enlarged view of part C in FIG. 10. As illustrated in FIG. 11, the first filtering device 1060 and one or more first disinfection devices 1032 may be provided at the air inlet 10122. The first filtering device 1060 may be configured to filter the air entering the cavity 10125 of the medical device 1000 from the air inlet 10122 to prevent pathogenic substances (e.g., bacteria, viruses) from entering the cavity 10125. Arrow A may refer to a direction of air flow. Since the one or more first disinfection devices 1032 are arranged between the air inlet 10122 and the first filtering device 1060, the air may flow from the air inlet 10122 to the first filtering device 1060 through the one or more disinfection devices 1032. In a process of air flowing to the first filtering device 1060, the air may first be disinfected by the one or more first disinfection devices 1032, and then flow to the first filtering device 1060 for further filtering.

FIG. 12 is an enlarged view of part D in FIG. 10. As illustrated in FIG. 12, the second filtering device 1070 and one or more second disinfection devices 1034 may be provided at the air outlet 10124. The second filtering device 1070 may be configured to filter the air flowing out of the cavity 10125 of the medical device 1000 from the air outlet 10124 to prevent pathogenic substances (e.g., bacteria, viruses) from entering an external space (e.g., an examination room) of the medical device 1000. Arrow A may refer to a direction of air flow. Since the second filtering device 1070 is arranged between the air outlet 10124 and the one or more second disinfection devices 1034, before the air is filtered, the air may be disinfected by the one or more second disinfection devices 1034 to further ensure that the discharged air does not carry any pathogenic substances.

Figure 13:
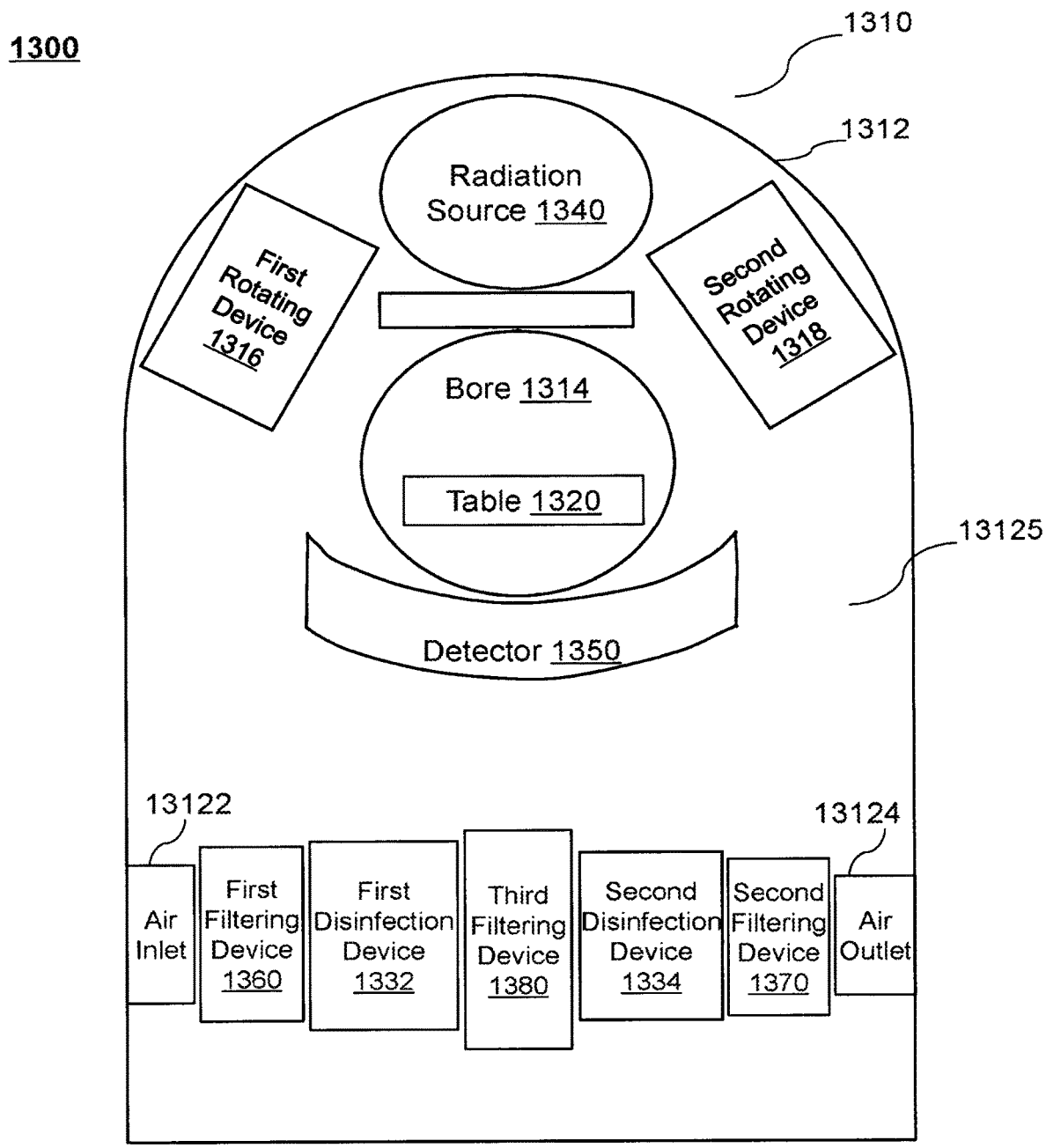
FIG. 13 is a schematic diagram illustrating an exemplary medical device according to some embodiments of the present disclosure.

FIG. 13 is a schematic diagram illustrating an exemplary medical device according to some embodiments of the present disclosure. The medical device 1300 may be the same as or similar to the medical device 900 as described in FIG. 9. For example, the medical device 1300 may include a gantry 1310, a table 1320, one or more disinfection devices (including a first disinfection device 1332, a second disinfection device 1334), a radiation source 1340, a detector 1350, and one or more filtering devices (including a first filtering device 1360, a second filtering device 1370, and a third filtering device 1380). The gantry 1210 may include a housing 1312, a bore 1314, a first rotating device 1316, and a second rotating device 1318. As another example, the housing 1312 of the gantry 1310 may form a cavity 13125 configured to accommodate one or more components (e.g., the radiation source 1340, the detector 1350) of the medical device 1300. The medical device 1300 may further include an air inlet 13122 and an air outlet 13124 arranged on the housing 1312. More descriptions for components of the medical device 1200 may be found elsewhere in the present disclosure (e.g., FIG. 2 or FIG. 9 and the descriptions thereof).

The first filtering device 1360 may be arranged between the air inlet 13122 and the first disinfection device 1332. The second filtering device 1370 may be arranged between the air outlet 13124 and the second disinfection device 1334. The third filtering device 1380 may be arranged in the cavity 13125 to filter the air in the cavity 13125, so as to prevent the spread of viruses and bacteria in the cavity 13125. In some embodiments, the first disinfection device 1332 may be arranged between the first filtering device 1360 and the third filtering device 1380. The second disinfection device 1334 may be arranged between the second filtering device 1370 and the third filtering device 1380. The third filtering device 1380 may be arranged between the first disinfection device 1332 and the second disinfection device 1334. The air outside the cavity 13125 may flow from the air inlet 13122 to the first disinfection device 1332 through the first filtering device 1360. In a process of air flowing to the first disinfection device 1332, the air may first be filtered by the first filtering device 1360, and then flow to the disinfection device 1332 for further disinfection. Moreover, the air may further filtered by the third filtering device 1380. The air in the cavity 13125 may be discharged from the air outlet 13124. Since the second filtering device 1370 is arranged between the air outlet 13124 and the second disinfection device 1334, before the air is filtered, the air may be disinfected by the second disinfection device 1334 to further ensure that the discharged air does not carry any pathogenic substances.

Figure 14:
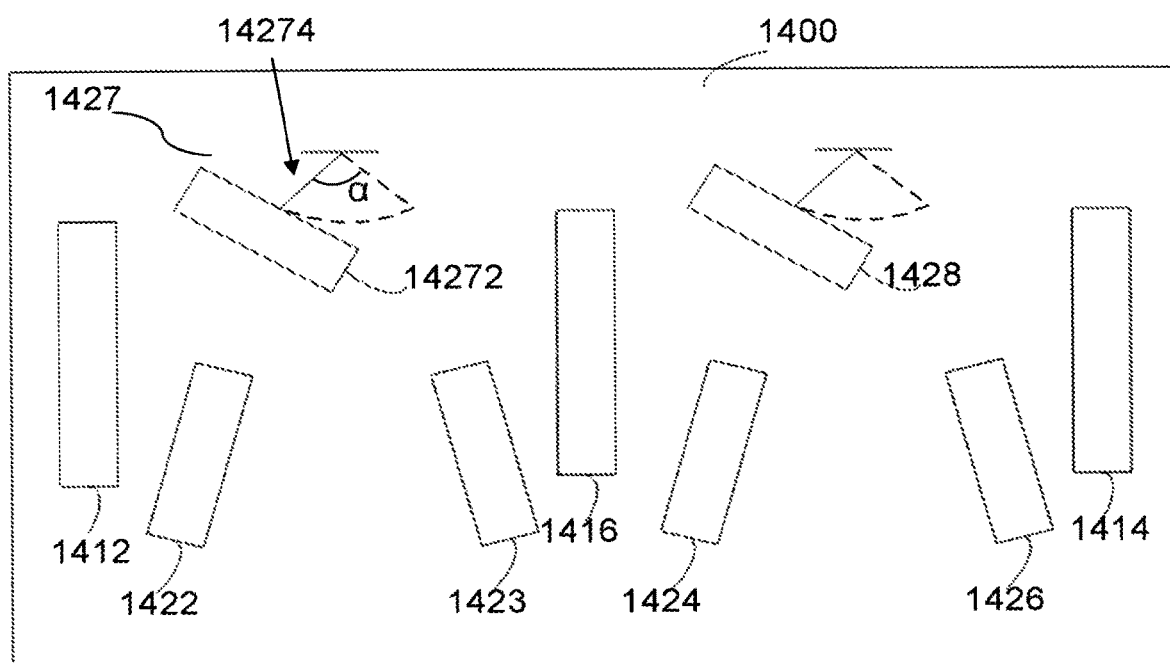
FIG. 14 is a schematic diagram illustrating an exemplary distribution of one or more filtering devices and one or more filtering disinfection devices according to some embodiments of the present disclosure.

It should be noted that a count of disinfection devices between each two components of the medical device 1300 may be equal to or more than two (as shown in FIG. 14).

FIG. 14 is a schematic diagram illustrating an exemplary distribution of one or more filtering devices and one or more filtering disinfection devices according to some embodiments of the present disclosure. As illustrated in FIG. 14, short rectangles indicate multiple disinfection devices 1422, 1423, 1424, 1426, 1427, and 1428. Long rectangles indicate multiple filtering devices including a first filtering device 1412, a second filtering device 1414, and a third filtering device 1416.

The multiple disinfection devices and the multiple filtering devices may be arranged in a cavity 1400 formed by a housing of a medical device. In some embodiments, different disinfection devices may have different orientations. For example, the disinfection devices 1422, 1423, and 1427 are arranged between the first filtering device 1412 and the third filtering device 1416. The orientation of the disinfection device 1422 may be toward the first filtering device 1412, and the orientation of the disinfection device 1423 may be toward the third filtering device 1416. The disinfection device 1427 may be arranged in rotation. The disinfection device 1427 may be rotated by a control instruction, so that the disinfection device 1427 can be toward the first filtering device 1412 and the third filtering device 1416 at different times, respectively. Similarly, as another example, the disinfection devices 1424, 1426, and 1428 may be arranged between the second filtering device 1414 and the third filtering device 1416. At least two of the orientations of the disinfection devices 1424, 1426, and 1428 may be different.

In some embodiments, the rotatable disinfection device 1427 may include a disinfection main portion 14272 and a movable portion 14274. The movable portion 14274 may include a slide, a slider (e.g., a wheel), and a connecting rod. The slide of the movable portion 14274 may be installed on the medical device (e.g., a table, the housing, etc., of the medical device). The disinfection main portion 14272 may be connected with the connecting rod of the movable portion 14274. The movable portion 14274 may move and/or rotate by a certain angle (e.g., as indicated by the angle $\alpha$) in response to receiving a rotating instruction, thereby driving the disinfection main portion 14272 to rotate. In such cases, a disinfection range of the disinfection device 1427 may be changed accordingly.

FIG. 15 is a schematic diagram illustrating an exemplary control device of a disinfection device according to some embodiments of the present disclosure. A control device 1500 may be provided on any one of the aforementioned medical devices.

As illustrated in FIG. 15, the control device 1500 may be communicated or connected with a disinfection device 1540 and/or a monitoring device 1530. The monitoring device 1530 may be arranged in an examination room where the medical device is located (e.g., on the medical device) and configured to acquire monitoring information associated with the medical device and/or an object to be scanned. The control device 1500 may be configured to control the disinfection device 1540 based on a control instruction (e.g., perform a disinfection operation). For example, a user may send a disinfection instruction to the control device 1500 to control the disinfection device 1540 to perform the disinfection operation. As another example, the control device 1500 may prevent the disinfection device 1540 from performing the disinfection operation in response to the monitoring information indicating that at least one object is within a preset range of the medical device. In other words, when there are one or more objects (e.g., doctors, patients, or any other medical staff) in the preset range of the medical device (e.g., the examination room), the disinfection device 1540 may be prohibited from working. For example, the control device 1500 may generate a turning off instruction to the disinfection device 1540 to turn off the disinfection device 1540 in response to the monitoring information indicating that at least one object is within the preset range of the medical device. As used herein, a range of the medical device may refer to an area including the medical device. For example, the area including the medical device may include a region where the medical is located and a region around the medical device. The medical device may be located on any position in the area (e.g., a center point, an edge point, etc., of the area). In some embodiments, the area may include a regular or irregular shape, such as a triangle, a rectangle, a circle, an ellipse, etc. In some embodiments, before sending the turning off instruction, the control device 1500 may detect a state of the disinfection device 1540. In response to determining that the disinfection device 1540 is in a working state, the control device 1500 may send the turning off instruction to the disinfection device 1540 to turn off the disinfection device 1540. In response to determining that the disinfection device 1540 is in an off state or a standby state, the control device 1500 may not send the turning off instruction to the disinfection device 1540.

In some embodiments, the preset range may be set according to a default setting of the medical device or preset by a user or operator via the terminal device. For example, the preset range may be a circular area centered on a location of the medical device with a specific radius. As another example, the preset range may be a rectangular area including the medical device with a specific size. As a further example, the preset range may be a whole region of the examination room.

In some embodiments, the monitoring device 1530 may include an imaging acquisition device and/or an audio acquisition device. Exemplary imaging acquisition devices may include an infrared camera, a gun camera, a dome camera, an integrated camera, a monocular camera, a binocular camera, a multi-view camera, a video recorder, etc. Exemplary audio acquisition devices may include a microphone. In some embodiments, the imaging acquisition device and the audio acquisition device may be integrated into a single component.

In some embodiments, the control device 1500 may acquire a disease diagnosis result indicating that whether the object to be scanned has an infectious disease, and generate a control instruction based on the disease diagnosis result. For example, the control device 1500 may generate a disinfection instruction in response to that the object has an infectious disease (e.g., corona virus disease 2019, COVID-19). In some embodiments, the control device 1500 may further control one or more parameters associated with the disinfection device 1540. For example, a user (e.g., an operator) may input the one or more parameters via a terminal device, the control device 1500 may generate a parameter adjustment instruction based on the input by the user and transmit the parameter adjustment instruction to the disinfection device 1540. As another example, the control device 1500 may determine a parameter adjustment instruction based on the monitoring information acquired by the monitoring device 1530. For example, when the monitoring information indicates that at least one object is within the preset range of the medical device, the control device 1500 may generate a parameter adjustment instruction to reduce a concentration of the disinfection medium of the disinfection device 1540. In some embodiments, the one or more parameters may include a disinfection intensity, a disinfection duration, a concentration of the disinfection medium of the disinfection device 1540, etc. In some embodiments, the control device 1500 may further include a disinfection intensity controller configured to adjust a disinfection intensity of the disinfection device 1540.

In some embodiments, the control device 1500 may include one or more hardware processors, such as a microcontroller, a microprocessor, a reduced instruction set computer (RISC), an application-specific integrated circuit (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof. The control device 1500 may be connected to the disinfection device 1540 and/or the monitoring device 1530 via a wired connection, a wireless connection, or a combination thereof. The wired connection may include, for example, an electrical cable, an optical cable, a telephone wire, or the like, or any combination thereof. The wireless connection may include a Bluetooth™ network, a local area network (LAN), a wide area network (WAN)), a near field communication (NFC) network, a ZigBee™ network, or the like, or any combination thereof. In some embodiments, the control device 1500 may be implemented in the medical device 110, the terminal device 130, the processing device 140, etc.

Specifically, as illustrated in FIG. 15, the control device 1500 may include a main controller 1512, a wireless controller 1514, and/or a control panel 1516. In some embodiments, each of the main controller 1512, the wireless controller 1514, and the control panel 1516 may correspond to the same or different disinfection intensity controllers (e.g., the disinfection intensity controllers 1522, 1524, or 1526) to control the disinfection intensity of the disinfection device 1540. In some embodiments, the disinfection intensity controller may generate a disinfection intensity control instruction based on information received from a terminal device or the monitoring device 1530. The disinfection intensity controller may transmit the disinfection intensity control instruction to the disinfection device 1540 to adjust a disinfection intensity of the disinfection device 1540. In some embodiments, the main controller 1512 may be provided on or integrated into a processing device of the medical device, the wireless controller 1514 may be provided on or integrated into a terminal device, and the control panel 1516 may be provided on a housing of the medical device (e.g., a housing of a gantry of the medical device). A user may input the control instruction via the main controller 1512, the wireless controller 1514, and/or the control panel 1516.

Figure 16:
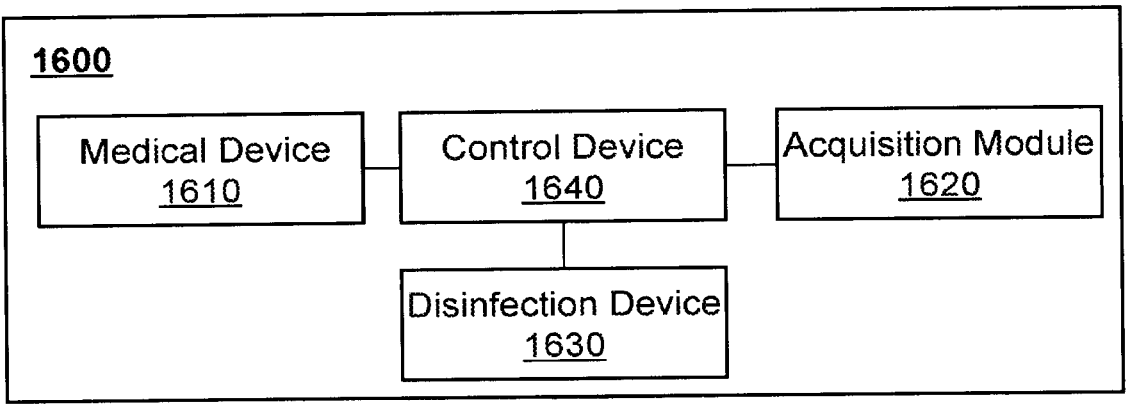
FIG. 16 is a block diagram illustrating an exemplary medical device control system according to some embodiments of the present disclosure.

FIG. 16 is a block diagram illustrating an exemplary medical device control system according to some embodiments of the present disclosure. As illustrated in FIG. 16, the medical device control system 1600 may include a medical device 1610, an acquisition module 1620, a disinfection device 1630, and a control device 1640. In some embodiments, the disinfection device 1630 may be integrated into or mounted on the medical device 1610. In such cases, the medical device 1610 including the disinfection device 1630 may be a medical device as described in FIGS. 2 to 15. For example, the medical device may include a gantry, a table, a radiation source, a detector, etc. The gantry may include a housing, a bore, one or more rotating devices, one or more support components, etc. More descriptions about a medical device including a disinfection device may be found elsewhere in the present disclosure (e.g., FIGS. 2 to 15 and the descriptions thereof).

In some embodiments, one or more components of the medical device control system 1600 may be communicated with each other via a wired or wireless connection. For example, the medical device 1610 may be connected with the control device 1640 via an electrical cable, an optical cable, etc. As another example, the control device 1640 may be communicated with the disinfection device 1630 and/or the acquisition module 1620 via a local area network (LAN), a wide area network (WAN)), a near field communication (NFC) network, a ZigBee™ network, etc.

The acquisition module 1620 may be configured to acquire information associated with the medical device 1610 and/or an object to be scanned, and transmit the acquired information to the control device 1640. In some embodiments, the information may include a scanning image of the object acquired by the medical device 1610 and/or other medical devices, medical information (e.g., a temperature) of the object, a state of the medical device 1610, user information around the medical device 1610 (e.g., body temperatures of objects in the surrounding environment of the medical device 1610), or the like, or any combination thereof. In some embodiments, the acquisition module 1620 may be realized by one or more communication interfaces. That is, the acquisition module 1620 may receive the information associated with the medical device 1610 and/or the object by connecting to a source device via the communication interfaces. For example, the acquisition module 1620 may be connected to a temperature measurement device, an image acquisition device, an audio acquisition device, a medical database, an imaging processing device of the medical device 1610, or the like, or any combination thereof. In some embodiments, the acquisition module 1620 may directly collect the information associated with the medical device 1610 and/or the object. That is, the acquisition module 1620 may be a device capable of directly collecting information. For example, the acquisition module 1620 may include a temperature measurement device, an image acquisition device, an audio acquisition device, or the like, or any combination thereof.

In some embodiments, the control device 1640 may determine whether the medical device 1610 needs to be disinfected based on the acquired information and generate a control instruction in response to determining that the medical device needs to be disinfected. Specifically, the control device 1640 may determine the medical device 1610 needs to be disinfected in response to that the acquired information satisfies a compliance condition. It should be noted that the compliance condition may be set according to actual application scenarios. For example, if the information includes temperatures of one or more objects, the compliance condition may include that at least one of the objects has a temperature greater than a temperature threshold. As another example, if the information includes images or audio associated with a range of the medical device 1610, the compliance condition may be that the images and/or audio include information indicating that the object has a cough or fever.

In some embodiments, the control instruction may include an instruction for controlling the medical device 1610 and/or the disinfection device. For example, the control instruction may include a scan control instruction for restricting at least part of functions of the medical device 1610 to work. Specifically, the control instruction may prevent the medical device 1610 from directly scanning or treating the next patient. In other words, the medical device 1610 may be locked in response to receiving the control instruction. Only after receiving an unlocking instruction, the medical device 1610 can perform scanning or treatment. As another example, the control instruction may include a disinfection instruction. In some embodiments, after the medical device 1610 is disinfected or receiving instruction information indicating that the medical device 1610 does not need to be disinfected, the control device 1640 may unlock the medical device 1610 to allow the medical device 1610 to perform scanning or treatment. In some embodiments, the control device 1640 may be implemented on the medical device 1610, a terminal device (e.g., the terminal device 130), a processing device (e.g., the processing device 140).

In some embodiments, the control device 1640 may further control one or more parameters associated with the disinfection device 1630. For example, a user (e.g., an operator) may input the one or more parameters via a terminal device, the control device 1640 may generate a parameter adjustment instruction based on the input by the user and transmit the parameter adjustment instruction to the disinfection device 1630. As another example, the control device 1640 may determine a parameter adjustment instruction based on the information acquired by the acquisition module 1620. For example, when the acquired information indicates that at least one object is within the preset range of the medical device 1610, the control device 1640 may generate a parameter adjustment instruction to reduce a concentration of the disinfection medium of the disinfection device 1630. In some embodiments, the one or more parameters may include a disinfection intensity, a disinfection duration, a concentration of the disinfection medium of the disinfection device, etc.

In some embodiments, the acquisition module 1620 may include or be communicated with a temperature measurement device configured to acquire temperature information of one or more objects (e.g., the object to be scanned, a doctor, a medical staff, etc.) within a first range of the medical device 1610. The temperature measurement device may be arranged at any position that can acquire the temperature information of the objects. For example, the temperature measurement device may be arranged on the medical device 1610. As another example, the temperature measurement device may be arranged on a wall of an examination room where the medical device 1610 is located. In some embodiments, the first range may be set according to a default setting of the medical device control system 1600 or preset by a user or operator via a terminal device. For example, the first range may be a circular area centered on a location of the medical device 1610 with a specified radius (e.g., 0.5 m, 1 m, 1.5 m, 2 m, etc.). As another example, the first range may be a rectangular area including the medical device 1610 with a specified size (e.g., area of 9 mm², length of 3 m, and width of 3 m). As a further example, the first range may be a whole space of the examination room. In some embodiments, the temperature measurement device may include an infrared imaging device. For example, the infrared imaging device may utilize an infrared detector for infrared imaging. The infrared detector may include a photon detector, a thermal detector, a cooled infrared detector, an uncooled infrared detector, a short wave infrared detector, a medium wave infrared detector, a long wave infrared detector, or the like, or any combination thereof. The infrared imaging device may capture infrared images of objects located in the first range of the medical device 1610 and generate temperatures of the one or more objects based on the infrared images. Then the infrared imaging device may transmit the acquired temperatures to the control device 1640 to determine whether at least one of the temperatures is greater than a temperature threshold, that is, to determine whether the information associated with the medical device 1610 and/or the object satisfies the compliance condition. In some embodiments, the temperature threshold may be set according to a default setting of the medical device control system 1600 or preset by a user or operator via the terminal device 130. For example, the temperature threshold may be set to 36.5° C., 36.8° C., 37° C., 37.3° C., 37.5° C., etc. In some embodiments, when the control device 1640 determines that the temperature of an object exceeds the temperature threshold, the object may be further measured by another thermometer (e.g., a portable handheld thermometer) to confirm that the temperature of the object exceeds the temperature threshold. In some embodiments, the temperature measurement device may directly determine whether the temperature of an object is greater than the temperature threshold, and transmit the determination result to the control device 1640. According to some embodiments of the present disclosure, by setting the temperature measurement device in the examination room, the temperature information of the objects in a relatively large range may be easily detected, which improves the disinfection performance of the medical device control system 1600.

In some embodiments, the acquisition module 1620 may include or be communicated with a monitoring device configured to capture monitoring information of a second range of the medical device 1610. In some embodiments, the second range may be the same as or different from the first range. For example, both the first range and the second range may be the examination room where the medical device 1610 is located. In some embodiments, the monitoring device may include an imaging acquisition device, an audio acquisition device, etc., as described in connection with the monitoring device 1530 described in FIG. 15. The monitoring device may transmit the acquired monitoring information to the control device 1640. The control device 1640 may identify the monitoring information acquired from the monitoring device and determine whether the medical device 1610 needs to be disinfected based on an identification result. For example, if the monitoring device includes an imaging acquisition device, the control device 1640 may receive images or videos associated the second range of the medical device 1610 from the imaging acquisition device, and determine whether image information in the images or videos indicates that at least one of the objects has a cough, that is, determine whether the information associated with the medical device 1610 and/or the object satisfies the compliance condition. As another example, if the monitoring device includes an audio acquisition device, the control device 1640 may receive an audio generated in the second range of the medical device 1610 from the audio acquisition device, and identify whether the audio includes target words, that is, determine whether the information associated with the medical device 1610 and/or the object satisfies the compliance condition. In some embodiments, the target words may include "temperature is greater than 37° C.," "temperature is abnormal," "has a fever," "has a cough," or the like, or any combination thereof. In some embodiments, the control device 1640 may determine whether the information associated with the medical device 1610 and/or the object satisfies the compliance condition based on the images and/or the audio according to an image recognition model and/or an audio recognition model. Exemplary image recognition models may include a linear regression model, a decision tree, a Naïve Bayes model, a support vector machine model, a K-nearest neighbor model, a random forest model, a neural network model, a voting model, a fuzzy logic model, etc. Exemplary audio recognition models may include a convolutional neutral network (CNN) model, a deep learning neutral network model, a hidden Markov model (HMM), etc. In some embodiments, the monitoring device may directly determine whether the monitoring information satisfies the compliance condition, and transmit the determination result to the control device 1640. According to some embodiments of the present disclosure, by setting the monitoring device to acquire image and/or audio information associated with the second range of the medical device 1610, suspicious information can be obtained in time, which improves the real-time disinfection performance of the medical device control system 1600.

In some embodiments, the acquisition module 1620 may be connected to a medical database. The medical database may include historical medical information of the object to be scanned. In some embodiments, the medical database may include medical information of the object to be scanned within a predetermined period (e.g., last hour, last day, last week, last month, etc.). In some embodiments, the historical medical information may include clinical diagnosis information of the object to be scanned. For example, if the object to be scanned is a patient, the clinical diagnosis information may include information in a radiology information system (RIS) and/or a hospital information system (HIS). In some embodiments, the clinical diagnosis information may include health status information of the patient and/or consultation information of the patient in a consultation record. The control device 1640 may determine whether the historical medical information has characteristic words using a text recognition model, that is, determine whether the information associated with the medical device 1610 and/or the object satisfies the compliance condition. In some embodiments, the characteristic words may include "infectious department," "infectious disease area," fever clinic," "have a fever in the past 14 days," "body temperature is higher than 36.5° C.," or the like, or any combination thereof. In some embodiments, the text recognition model may include a classifier for natural language recognition, an efficient and accuracy scene text detection pipeline (EAST) model, a seglink model, a single shot multibox detector (SSD), a you only look once version 3 (YOLOV3), or the like, or any combination thereof.

In some embodiments, the acquisition module 1620 may directly determine whether the historical medical information has the characteristic words, and transmit the determination result to the control device 1640. According to some embodiments of the present disclosure, by identifying and/or judging the historical medical information in the medical database, the acquisition module 1620 can improve the accuracy of judging whether the patient is infected or not, thereby improving the accuracy of judging whether the medical device 1610 needs to be disinfected.

In some embodiments, if the medical device 1610 includes an imaging device (e.g., a CT device, an IGRT device, etc.), the acquisition module 1620 may be connected with an image processing device (e.g., the processing device 140) of the imaging device 1610 to acquire one or more images of the scanned object. The image processing device may generate or reconstruct the one or more images of a region of interest (ROI) of the object based on scan data acquired during the scanning of the object and analyze the generated images. The acquisition module 1620 may directly acquire an analysis result from the image processing device, and transmit the analysis result to the control device 1640. For example, the generated images may include a lung image of the object. The control device 1640 may receive the generated images form the image processing device, and determine whether the object has an infectious disease based on the generated images, that is, determine whether the information associated with the medical device 1610 and/or the object satisfies the compliance condition. In some embodiments, the control device 1640 may determine whether the object has an infectious disease based on the generated images according to a depth learning model that is generated based on neural network training combined with a large number of image identification samples. In some embodiments, the image processing device may directly determine whether the object has an infectious disease based on the generated images, and transmit the determination result to the acquisition module 1620. According to some embodiments of the present disclosure, by directly obtaining and/or identifying the analysis result from the image processing device, the acquisition module 1620 can improve the accuracy of judging whether the patient is infected or not, thereby improving the accuracy of judging whether the medical device 1610 needs to be disinfected.

In some embodiments, the medical device control system 1600 may further include a medical device controller configured to determine a state of the medical device 1610. The control device 1640 may determine whether the medical device needs to be disinfected based on the information acquired by the acquisition module 1620 and the state of the medical device 1610. More descriptions regarding the medical device controller may be found elsewhere in the prevent disclosure (e.g., FIG. 17, and the descriptions thereof). In some embodiments, the medical device control system 1600 may further include an alarm device configured to generate alarm information in response to determining that the medical device 1610 needs to be disinfected. More descriptions regarding the alarm device may be found elsewhere in the prevent disclosure (e.g., FIG. 18 and the descriptions thereof).

According to some embodiments of the present disclosure, by setting the acquisition module 1620 to acquire the information of the medical device 1610 and/or the object, and the control device 1640 to determine whether the medical device 1610 needs to be disinfected based on the information acquired by the acquisition module 1620, it can automatically determine whether the medical device 1610 needs to be disinfected during scanning of a patient, thereby reducing the probability of cross-infection between different patients and/or doctors.

It should be noted that the above description of the medical device control system 1600 is merely provided for the purposes of illustration, and not intended to limit the scope of the present disclosure. For persons having ordinary skills in the art, multiple variations and modifications may be made under the teachings of the present disclosure. In some embodiments, the control device 1640 may further be configured to control one or more components (e.g., the gantry, the table, the radiation source, the detector, etc.) of the medical device 1610. In some embodiments, the control device 1640 and the control device 1500 described in FIG. 15 may be integrated into a single component.

Figure 17:
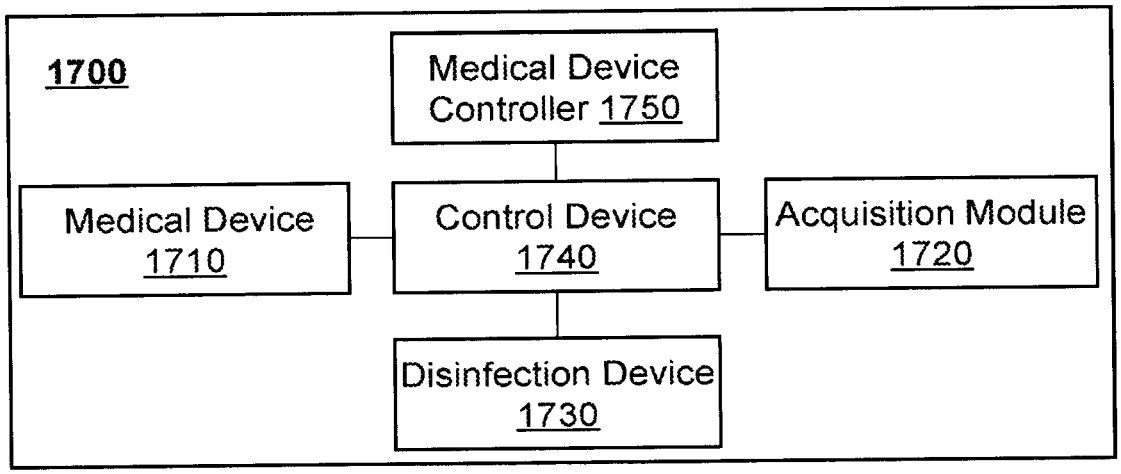
FIG. 17 is a block diagram illustrating an exemplary medical device control system according to some embodiments of the present disclosure.

FIG. 17 is a block diagram illustrating an exemplary medical device control system according to some embodiments of the present disclosure. The medical device control system 1700 may be the same as or similar to the medical device control system 1600 as described in FIG. 16. For example, as illustrated in FIG. 17, the medical device control system 1700 may include a medical device 1710, an acquisition module 1720, a disinfection device 1730, and a control device 1740. As another example, the disinfection device 1730 may be integrated into the medical device 1710. More descriptions for components of the medical device control system 1700 may be found elsewhere in the present disclosure (e.g., FIG. 16 and the descriptions thereof).

The medical device control system 1700 may further include a medical device controller 1750 configured to acquire a state of the medical device 1710. In some embodiments, the state of the medical device 1710 may include a shutdown state, a standby state, a working state, a routine maintenance state, or the like, or any combination thereof. In some embodiments, the medical device controller 1750 may be connected with the control device 1740 via a wired or wireless connection. In some embodiments, the medical device controller 1750 may be integrated into the control device 1740.

The control device 1740 may determine whether the medical device 1710 needs to be disinfected based on information acquired by the acquisition module 1720 and the state of the medical device 1710 determined by the medical device controller 1750. In some embodiments, when the information acquired by the acquisition module 1720 satisfies a compliance condition and the medical device 1710 is in a standby state or a shutdown state, the control device 1740 may determine that the medical device 1710 needs to be disinfected. The control device 1740 may generate a control instruction for restricting at least part of functions of the medical device 1710 to work in response to determining that the medical device 1710 needs to be disinfected. In some embodiments, the at least part of functions of the medical device 1710 may include performing scanning, emitting radiation rays, moving the table, or the like, or any combination thereof. In some embodiments, when the information acquired by the acquisition module 1720 satisfies the compliance condition and the medical device 1710 is in a working state or in a routine maintenance state of a radiation source of the medical device 1710, the control device 1740 may determine that the medical device 1710 does not need to be disinfected right now. The control device 1740 may generate the control instruction for restricting the at least part of functions of the medical device 1710 to work when the scan is completed. According to some embodiments of the present disclosure, by setting the medical device controller 1750, the control device 1740 may not interfere with the normal scanning of the medical device 1710.

Figure 18:
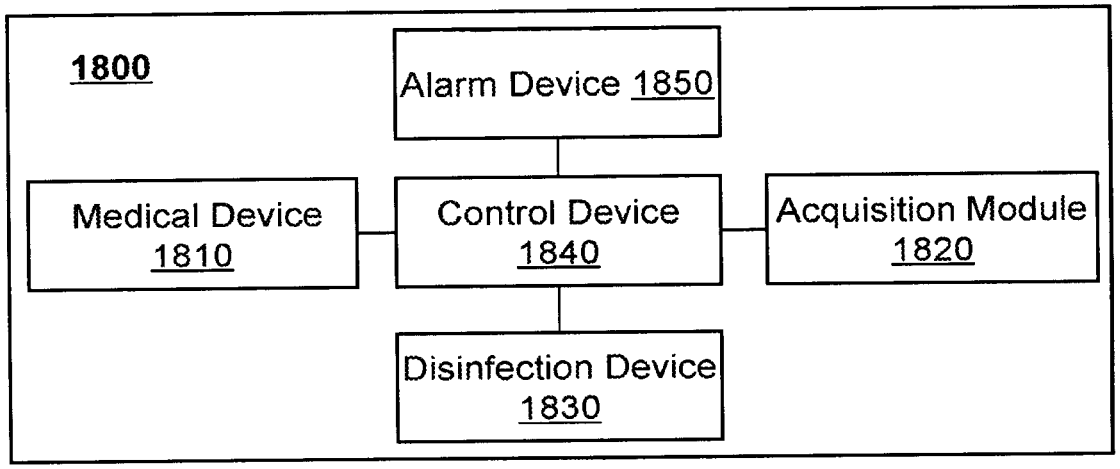
FIG. 18 is a block diagram illustrating an exemplary medical device control system according to some embodiments of the present disclosure.

FIG. 18 is a block diagram illustrating an exemplary medical device control system according to some embodiments of the present disclosure. The medical device control system 1800 may be the same as or similar to the medical device control system 1600 as described in FIG. 16. For example, as illustrated in FIG. 18, the medical device control system 1800 may include a medical device 1810, an acquisition module 1820, a disinfection device 1830, and a control device 1840. As another example, the disinfection device 1830 may be integrated into the medical device 1810. More descriptions for components of the medical device control system 1800 may be found elsewhere in the present disclosure (e.g., FIG. 16 and the descriptions thereof).

The medical device control system 1800 may further include an alarm device 1850 configured to generate and/or broadcast an alarm signal in response to the determining that the medical device 1810 needs to be disinfected. In some embodiments, the alarm signal may be in form of text, audio, image, animation, or the like, or any combination thereof. The alarm signal may remind a user (e.g., a doctor) to interact with the medical device control system 1800. In some embodiments, the user may interact with the medical device control system 1800 via the alarm device 1850, the control device 1840, etc. For example, when the user receives the alarm signal, the user may input information indicating that or confirming that the medical device 1810 needs or does not need to be disinfected via the alarm device 1850. After the alarm device 1850 receives the information input by the user, the alarm device 1850 may stop broadcasting the alarm signal. As another example, when the user receives the alarm signal, the user may input information instructing to perform disinfection via the control device 1840. The control device 1840 may generate a disinfection instruction based on the input by the user.

In some embodiments, the alarm device 1850 may further be configured to obtain disinfection progress information of the disinfection device 1830 and transmit the obtained disinfection progress information to the control device 1840. In some embodiments, the disinfection progress information may indicate that whether the medical device 1810 needs to be disinfected, or whether the disinfection is completed. For example, the alarm device 1850 may include an acquisition unit directly connected with the disinfection device 1830, the disinfection device 1830 may send information indicating that the disinfection is completed to the acquisition unit after the disinfection is completed. The alarm device 1850 may generate alarm information to remind the user in response to receiving the information that the disinfection is completed. In some embodiments, the control device 1840 may allow at least part of functions of the medical device 1810 to work (e.g., allow the medical device 1810 to perform a scan) in response to the disinfection progress information indicating that the disinfection is completed or the medical device 1810 does not need to be disinfected. In some embodiments, the alarm device 1850 may be connected with the control device 1840 via a wired or wireless connection. In some embodiments, the medical device controller 1850 may be integrated into the control device 1840. According to some embodiments of the present disclosure, by setting the alarm device 1850, the user may be reminded to interact with the medical device control system 1800, which ensures that the medical device 1810 can be successfully disinfected and enables the medical device 1810 to start working in time after the disinfection is completed.

Figure 19:
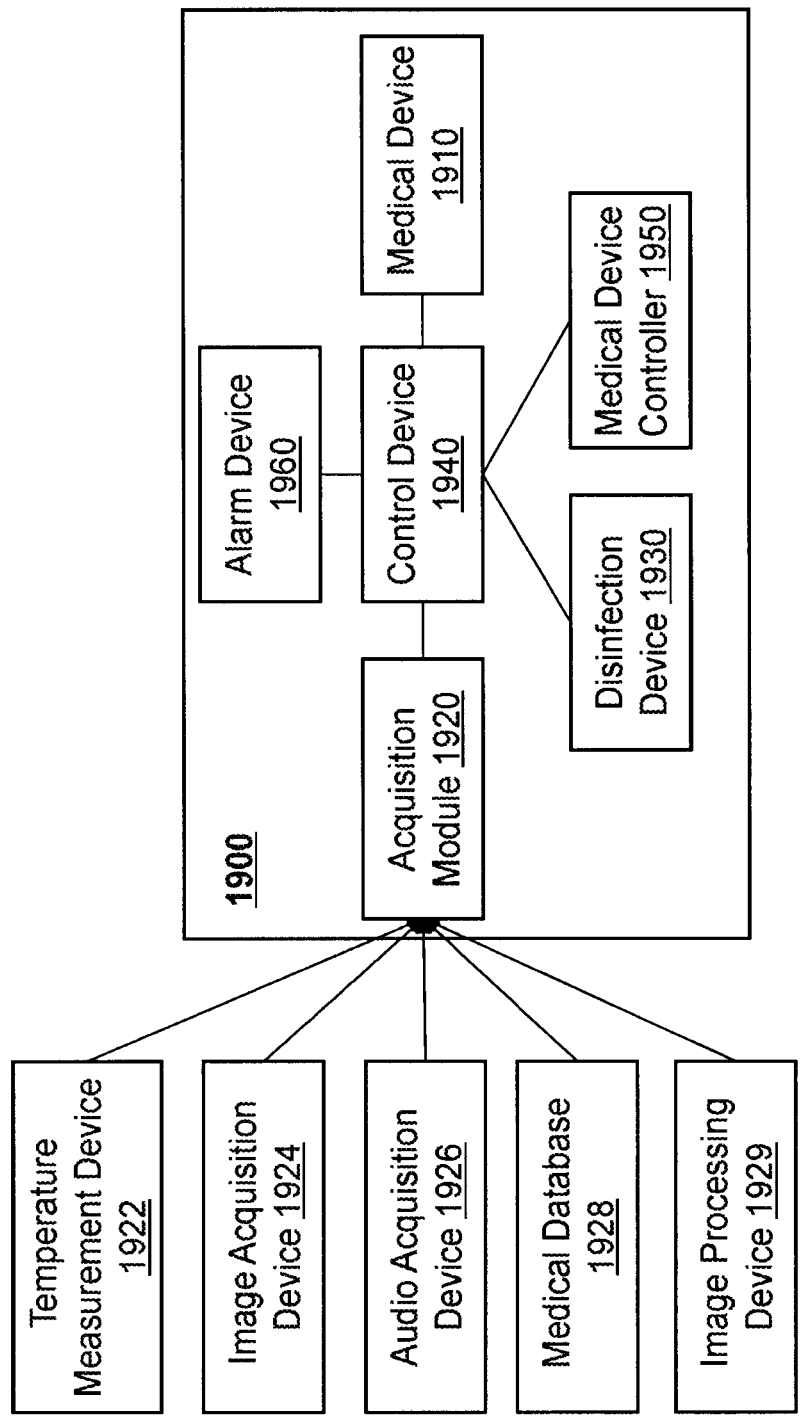
FIG. 19 is a block diagram illustrating an exemplary medical device control system according to some embodiments of the present disclosure.

FIG. 19 is a block diagram illustrating an exemplary medical device control system according to some embodiments of the present disclosure. The medical device control system 1900 may be the same as or similar to the medical device control system 1600 as described in FIG. 16. For example, as illustrated in FIG. 19, the medical device control system 1900 may include a medical device 1910, an acquisition module 1920, a disinfection device 1930, and a control device 1940. As another example, the disinfection device 1930 may be integrated into the medical device 1910. More descriptions for components of the medical device control system 1900 may be found elsewhere in the present disclosure (e.g., FIG. 16 and the descriptions thereof).

The medical device control system 1900 may further include a medical device controller 1950 and an alarm device 1960 as described in FIGS. 17 and 18. The acquisition module 1920 may be connected with one or more information resources including a temperature measurement device 1922, an image acquisition device 1924, an audio acquisition device 1926, a medical database 1928, and an image processing device 1929. The control device 1940 may acquire information associated with the medical device 1910 and/or an object to be scanned from the one or more information resources connected with the acquisition module 1920. The control device 1940 may determine whether the medical device 1910 needs to be disinfected based on the information from each information resource. As long as the control device 1940 determines that a piece of information satisfies the corresponding compliance condition, the alarm device 1960 may be triggered to generate and/or broadcast an alarm signal, thereby realizing the interaction between the medical device control system 1900 and a user (e.g., a medical staff) regarding whether the medical device 1910 needs to be disinfected.

Figure 20:
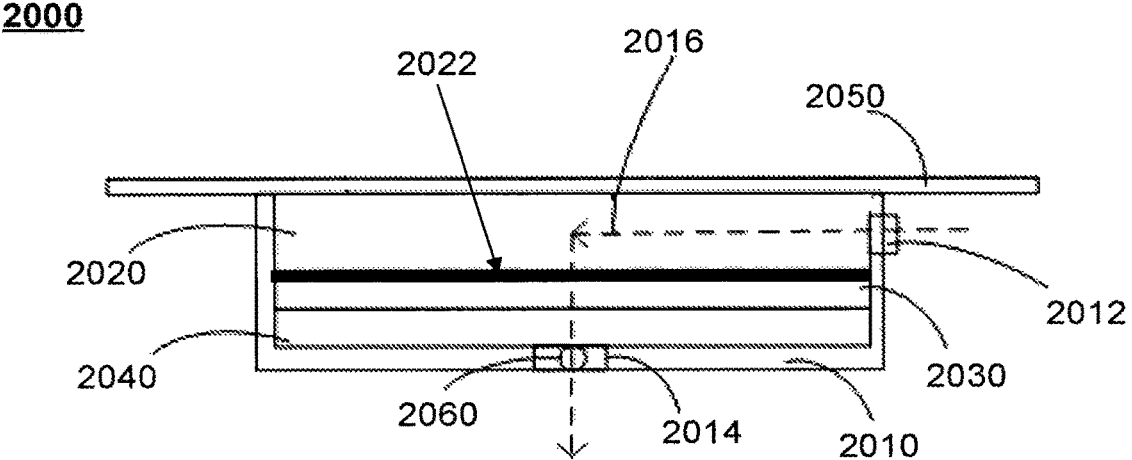
FIG. 20 is a schematic diagram illustrating an exemplary air purification device according to some embodiments of the present disclosure.

FIG. 20 is a schematic diagram illustrating an exemplary air purification device according to some embodiments of the present disclosure. In some embodiments, an air purification device 2000 may be arranged in a medical system including a medical cabin (or examination room) configured to accommodate medical resources such as a medical device (e.g., an imaging device, a treatment device, etc.). The air purification device 2000 may be arranged on different positions in the medical cabin. For example, the air purification device 2000 may be arranged on a top surface, a bottom surface, and/or sidewalls of the medical cabin via a fixing device 2050. In some embodiments, the air purification device 2000 may also be arranged on the outside of the medical cabin, such as an outer top surface, an outer bottom surface, and/or outer side walls of the medical cabin. The air purification device 2000 may be in flow communication with the inside of the medical cabin via multiple pipes. In some embodiments, the air purification device 2000 may be arranged in the medical cabin through a movable structure, so that the air purification device 2000 can be moved to different positions according to practical needs. For example, the air purification device 2000 may be connected with the movable structure via the fixing device 2050.

As illustrated in FIG. 20, the air purification device 2000 may include a housing 2010, a draught fan 2020, a filtering device 2030, and a disinfection device 2040.

The housing 2010 may form a cavity to accommodate the draught fan 2020, the filtering device 2030, and the disinfection device 2040. In some embodiments, the housing 2010 may be provided with an air inlet 2012 and an air outlet 2014. Both the air inlet 2012 and the air outlet 2014 may be in flow communication with the inside of the medical cabin. An air duct 2016 (as indicated by the dotted arrow illustrated in FIG. 20) may be formed between the air inlet 2012 and the air outlet 2014. The air entering the air inlet 2012 may be discharged by the draught fan 2020 through the air outlet 2014. The filtering device 2030 and/or the disinfection device 2040 may be arranged between the air inlet 2012 and the air outlet 2014 (i.e., in the air duct 2016). If the draught fan 2020 is turned on, the air in the medical cabin may enters the air duct 2016 of the air purification device 2000 through the air inlet 2012. The air may then be filtered by the filtering device 2030 and disinfected by the disinfection device 2040, and finally enters the medical cabin through the air outlet 2014. In such cases, the air in the medical cabin may be continually purified.

In some embodiments, the air inlet 2012 and/or the air outlet 2014 may be provided with an air flow direction control device configured to control an air flow direction of air. For example, a first air flow direction control device arranged at the air inlet 2012 may control air to flow from the medical cabin to the cavity of the air purification device 2000, and a second air flow direction control device arranged at the air outlet 2014 may control air to flow from the cavity of the air purification device 2000 to the medical cabin. As another example, the air flow direction control device 2060 arranged at the air outlet 2014 may control the air in the cavity of the air purification device 2000 to flow toward different directions of the medical cabin. In some embodiments, the air flow direction control device 2060 may include a valve, a louver fan, an air deflector, etc., capable of controlling the air flow direction. In some embodiments, the air inside the housing 2010 may circulate with the air outside the medical cabin through the air inlet 2012 and the air outlet 2014. For example, at least portion of the air outlet 2014 may be in flow communication with the air in the medical cabin, and the remaining portion of the air outlet 2014 may be in flow communication with one or more vents arranged on a top surface, a bottom surface, and/or inner side walls of the medical cabin. In other words, the air outlet 2014 may be in flow communication with the air outside the medical cabin. The air flow direction control device 2060 arranged at the air outlet 2014 may control the air flow in at least two directions, one of which is flow from the cavity of the air purification device 2000 to the medical cabin, and the other is flow from the cavity of the air purification device 2000 to the outside of the medical cabin.

In some embodiments, for different scenarios, the air flow direction control device 2060 may be adjusted according to the air circulation of the medical cabin. For example, when the medical cabin is used frequently (e.g., during an epidemic), a door of the medical cabin may open and close frequently, and a frequency of air convection inside and outside the medical cabin may be relatively high. In such cases, the air flow direction control device 2060 may be controlled to control an air flow direction from the air outlet 2014 to the outside of the medical cabin. At this time, the air in the medical cabin may enter the cavity of the air purification device 2000 through the air inlet 2012 and then be discharged out of the medical cabin through the air outlet 2014, thereby forming a negative pressure in the medical cabin. When the door is opened, the air outside the medical cabin may enter the medical cabin under the negative pressure, thereby introducing fresh air outside the medical cabin, and further improving the air quality in the medical cabin. Conversely, when the medical cabin is seldom used, the frequency of air convection inside and outside the medical cabin may be relatively low. In such cases, the air flow direction control device 2060 may be controlled to control an air flow direction just from the air outlet 2014 to the medical cabin. The air purification device 2000 may just purify (e.g., filter and/or disinfect) the air in the medical cabin. In some embodiments, the air outlet 2014 may be divided into a plurality of small air outlets to improve the air discharge effect.

In some embodiments, the air inlet 2012 and the air outlet 2014 may be arranged at any appropriate position of the air purification device 2000, as long as the air inlet 2012 and the air outlet 2014 are relatively independent and arranged at intervals. In some embodiments, the air inlet 2012 and the air outlet 2014 may be arranged on a same surface of the housing 2010 (or the air purification device 2000). For example, the air inlet 2012 and the air outlet 2014 may be arranged at two different positions of a top surface of the air purification device 2000 and separated by a predetermined distance. As another example, the air inlet 2012 and the air outlet 2014 may be arranged close to each other. An angle between a first air flow direction of the air controlled by a first air flow direction control device of the air inlet 2012 and a second air flow direction of the air controlled by a second air flow direction control device of the air outlet 2014 may be less than an angle threshold (e.g., 90°, 60°, 45°, 30°, etc.). In some embodiments, an angle between the first orientation and the second orientation may be greater than an angle threshold to prevent purified air discharged from the air outlet 2014 from being sucked into the air inlet 2012 again. In some embodiments, the air inlet 2012 and the air outlet 2014 may be arranged at different inner surfaces of the housing 2010 (or the air purification device 2000). For example, the air inlet 2012 may be arranged on a sidewall of the air purification device 2000, and the air outlet 2014 may be arranged on a top surface of the air purification device 2000. As another example, the air inlet 2012 may be arranged on a top surface of the air purification device 2000, and the air outlet 2014 may be arranged on a sidewall of the air purification device 2000. As a further example, the air inlet 2012 and the air outlet 2014 may be arranged on different sidewalls (e.g., opposite sidewalls) of the air purification device 2000.

Figures 22, 23:
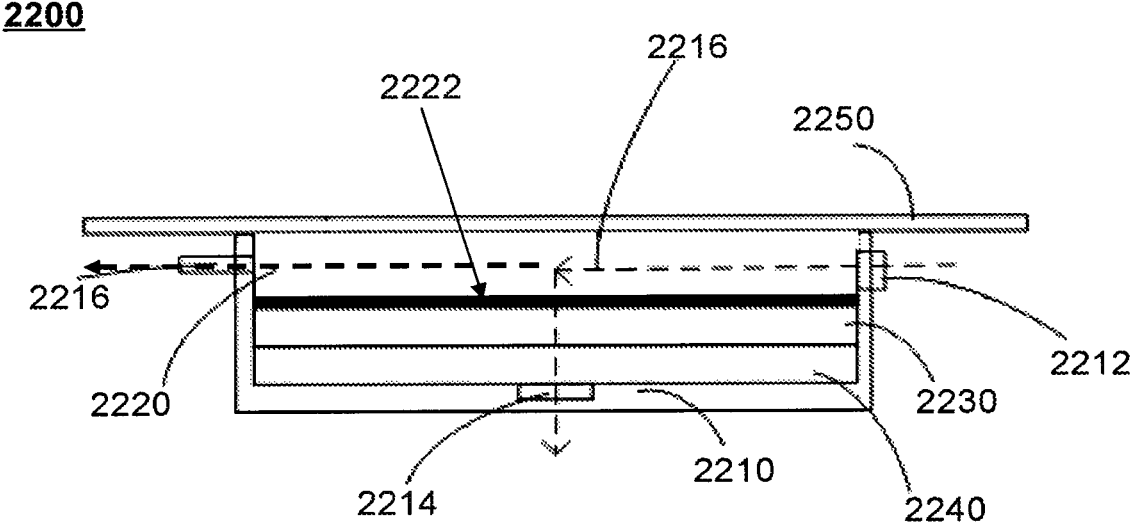
FIG. 22 is a schematic diagram illustrating an exemplary air purification device according to some embodiments of the present disclosure.
FIG. 23 is a block diagram illustrating an exemplary air purification system according to some embodiments of the present disclosure.

In some embodiments, the housing 2010 may be provided with two or more air inlets and/or air outlets (as shown in FIG. 22).

The filtering device 2030 may be configured to filter the air passing through the filtering device 2030. For example, the filtering device may filter out at least part of particles (e.g., dust), bacteria, and/or viruses in the air. In some embodiments, a dust-proof net 2022 may be mechanically arranged between the air inlet 2012 and the filtering device 2030 to improve a service life of the filtering device 2030. In some embodiments, the dust-proof net 2022 may be arranged between the air inlet 2012 and the draught fan 2020. In some embodiments, the dust-proof net 2022 may include a non-metal net and/or a metal net. Exemplary non-metal nets may include a nylon net, a cotton net, etc. Exemplary metal nets may include an iron net, an aluminum net, etc. In some embodiments, the air purification device 2000 may include two or more filtering devices to achieve different filtering effects. More descriptions regarding the filtering device may be found elsewhere in the present disclosure (e.g., FIG. 9 and FIG. 21 and the descriptions thereof).

The disinfection device 2040 may be configured to disinfect the air passing through the disinfection device 2040. In some embodiments, the air purification device 2000 may include two or more disinfection devices to achieve different disinfection effects. More descriptions regarding the disinfection device may be found elsewhere in the present disclosure (e.g., FIG. 2 and FIG. 21 and the descriptions thereof).

Figure 24A:
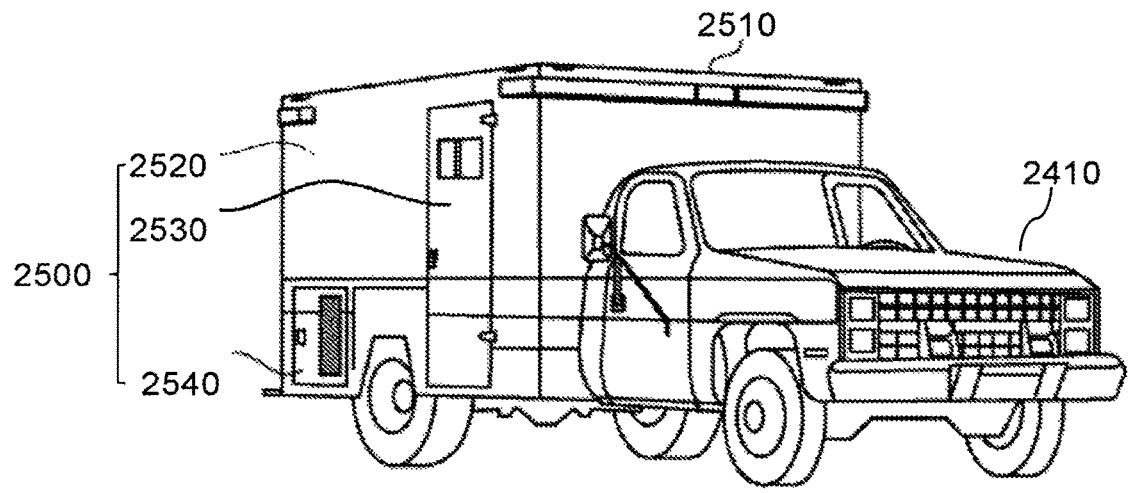
FIGS. 24A and 24B are schematic diagrams illustrating an exemplary in-vehicle medical system from different perspectives according to some embodiments of the present disclosure.
Figure 24B:
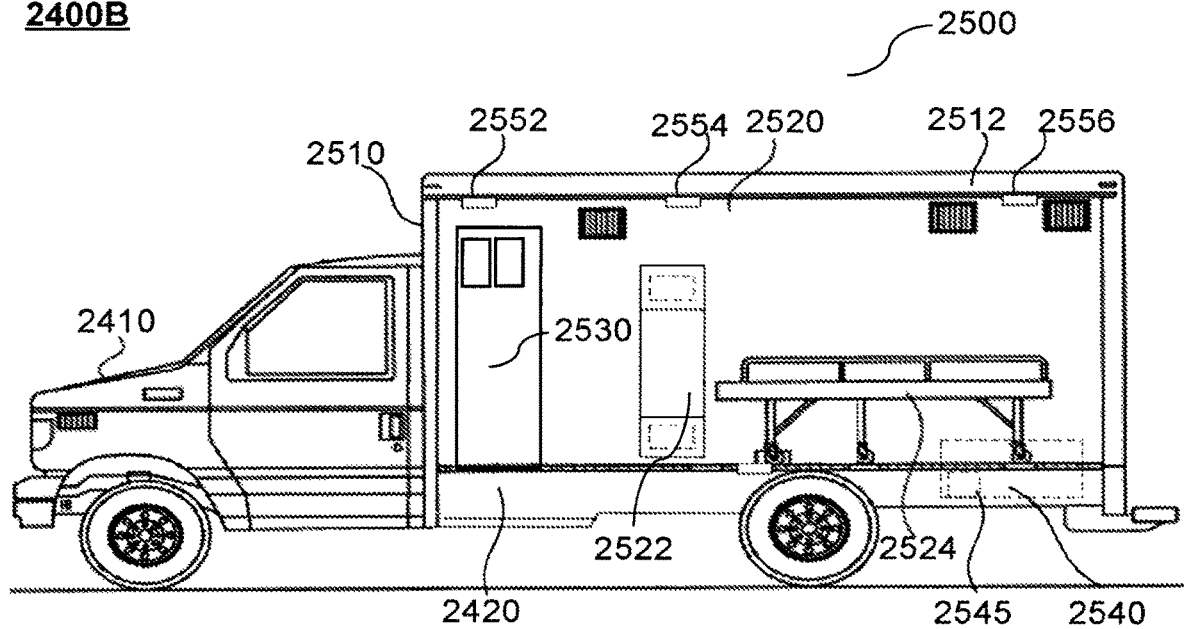

In some embodiments, the air purification device 2000 may further include one or more air quality sensors each of which is configured to detect an air quality of the air in the medical cabin (as shown in FIG. 24B). The air purification device 2000 may be controlled according to the air quality in the medical cabin. More descriptions regarding the air quality sensor may be found elsewhere in the present disclosure (e.g., FIG. 24B and the descriptions thereof).

In some embodiments, the air purification device 2000 may be connected with a control device configured to control the air purification device 2000. For example, the control device may turn on or turn off the air flow direction control device 2060, the disinfection device, 2040, and/or the draught fan 2020. As another example, the control device may adjust the air flow direction through the air flow direction control device 2060. As a further example, the control device may change a wind speed of the draught fan 2020. In some embodiments, the control device may realize automatic control according to an opening frequency of the door of the metal cabin. For example, if the opening frequency of the door exceeds a threshold value, the control device may control the air to be discharged from the air outlet 2014 to the outside of the medical cabin only. If the opening frequency of the door is less than the threshold value, the control device may control the air to be discharged from the air outlet 2014 to the medical cabin. In some embodiments, the control device may be implemented on a terminal device to enable users to control the air purification device 2000. More descriptions about the control device may be found elsewhere in the present disclosure (e.g., FIG. 23 and the descriptions thereof).

Figure 21:
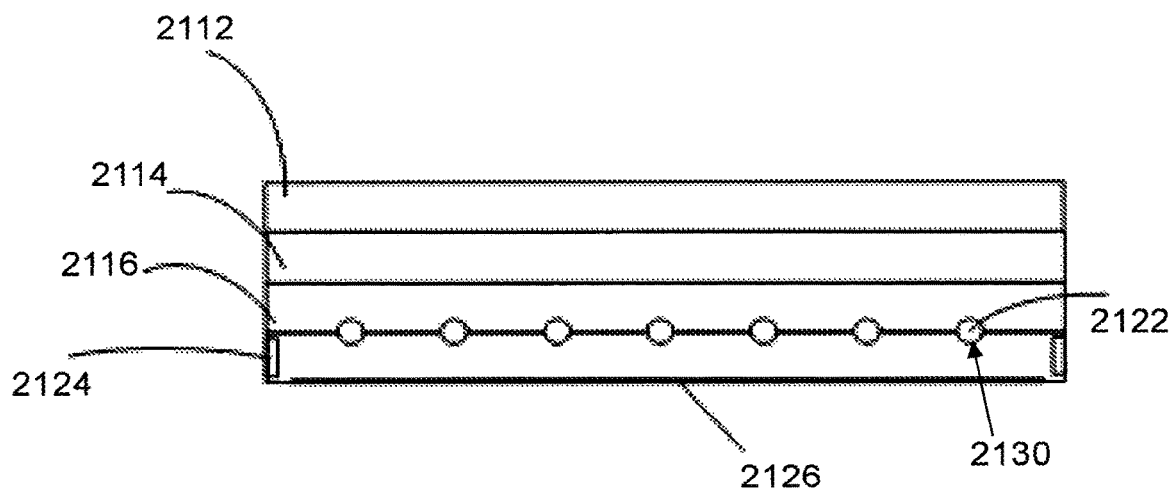
FIG. 21 is a schematic diagram illustrating an exemplary filtering device and an exemplary disinfection device of an air purification device according to some embodiments of the present disclosure.

FIG. 21 is a schematic diagram illustrating an exemplary filtering device and an exemplary disinfection device of an air purification device according to some embodiments of the present disclosure.

As illustrated in FIG. 21, an air purification device (e.g., the air purification device 2000) may include a first filtering device 2112, a second filtering device 2114, and a third filtering device 2116. In some embodiments, the filtering devices may have different filtering effects. In other words, different filtering devices may filter different particles or particles of different sizes. In some embodiments, different grades of filter nets of the filtering devices may be selected according to the requirements for air purification in different occasions. For example, in the case of a relatively high purification requirement, an electrostatically charged melt blown ultrafine fiber non-woven fabric may be used to effectively filter bacterial particles smaller than 1 µm. In some embodiments, the first filtering device 2112 may be configured to filter particles (e.g., large particles such as hair) larger than a first size. For example, the first filtering device 2112 may filter suspended particles of more than 5 µm and sedimentation particles of more than 10 µm. In some embodiments, the first size may be 5 µm, 10 µm, 15 µm, 20 µm, 25 µm, etc. In some embodiments, the first filtering device 2112 may include a plate type filtering device, a foldable type filtering device, a bag type filtering device, or the like, or any combination thereof. In some embodiments, an outer housing of the first filtering device 2112 may include a paper housing, an aluminum housing, a galvanized iron housing, or the like, or any combination thereof. In some embodiments, a filter material of the first filtering device 2112 may include a non-woven fabric, a nylon mesh, a metal mesh, or the like, or any combination thereof.

The second filtering device 2114 may be configured to filter particles between the first size and a second size. In some embodiments, the second size may be 5 µm, 4 µm, 3 µm, 2 µm, 1 µm, 0.5 µm, etc. In some embodiments, a type of the second filtering device 2114 may be the same as or different from the first filtering device 2112. For example, the second filtering device 2114 may also include a plate type filtering device, a foldable type filtering device, a bag type filtering device, etc. In some embodiments, an outer housing of the second filtering device 2114 may include a cold plate sprayed plastic housing, an aluminum alloy housing, a galvanized steel plate housing, or the like, or any combination thereof. In some embodiments, a filter material of the second filtering device may include a non-woven fabric, a nylon mesh, a glass fiber, etc., with a filter particle size between the first size and the second size. In some embodiments, the second filtering device 2114 may also be configured to filter gas molecule such as formaldehyde, sulfur dioxide, etc. In some embodiments, the second filtering device 2114 may include an activated carbon filter, a photocatalyst filter, etc.

The third filtering device 2116 may be configured to filter particles smaller than the second size. In some embodiments, the third filtering device 2116 may include a HEPA filter. In some embodiments, the first filtering device 2112, the second filtering device 2114, and/or the third filtering device 2116 may be detachably arranged in a housing of the air purification device, so as to facilitate the replacement and maintenance of the filtering devices (e.g., filter nets and/or filter media/materials).

In some embodiments, the air purification device may include one or more first disinfection devices 2122, and one or more second disinfection devices 2124. The first disinfection devices 2122 and the second disinfection devices 2124 may have different disinfection effects. For example, the first disinfection devices 2122 may include multiple ultraviolet disinfection devices such as a UVA lamp, a UVC lamp, etc. The second disinfection devices 2124 may include multiple ozone disinfection devices. The ultraviolet disinfection devices may be arranged at the air outlet side of the filtering device 2116. In some embodiments, a plurality of grooves 2130 may be provided between the first disinfection devices 2122 and the third filtering device 2116 for installing the first disinfection device 2122 (e.g., the ultraviolet disinfection devices). In some embodiments, the plurality of grooves 2130 may be arranged at equal intervals or randomly (e.g., randomly set by a user). The second disinfection devices 2124 (e.g., the ozone disinfection devices) may be arranged on the inner sidewall of the housing 2010. For example, when air enters an air duct of the air purification device, the ozone disinfection devices may release ozone to disinfect the air entering the air duct.

In some embodiments, in order to improve the disinfection effect, the air purification device may further include a third disinfection device that has a different disinfection effect than the first disinfection devices and the second disinfection devices, such as a titanium dioxide photocatalyst disinfection device.

FIG. 22 is a schematic diagram illustrating an exemplary air purification device according to some embodiments of the present disclosure. As illustrated in FIG. 22, an air purification device 2200 may be the same as or similar to the air purification device 2000 as described in FIG. 20. For example, the air purification device 2200 may include a housing 2210, a draught fan 2220, a filtering device 2230, and a disinfection device 2240. As another example, the air purification device 2200 may be located inside the medical cabin and arranged on a top surface, a bottom surface, and/or sidewalls of a medical cabin via a fixing device 2250. As a further example, a dust-proof net 2222 may be mechanically arranged between an air inlet 2212 and the filtering device 2230 to improve a service life of the filtering device 2230. More descriptions for components of the air purification device 2200 may be found elsewhere in the present disclosure (e.g., FIG. 20 and the descriptions thereof).

The housing 2210 may be provided with at least one air inlet 2212 and one or more air outlets (e.g., a first air outlet 2214, a second air outlet 2216). An air duct 2216 (as indicated by the dotted arrow illustrated in FIG. 22) may be formed between the air inlet 2212 and each air outlet. The air entering the air inlet 2212 may be discharged by the draught fan 2220 through the first air outlet 2214 and/or the second air outlet 2216.

The first air outlet 2214 and the second air outlet 2216 may be arranged independently, and air flow directions of the first air outlet 2214 and the second air outlet 2216 may be different. For example, the first air outlet 2014 may be in flow communication with the inside of the medical cabin, and a first air flow direction of the first air outlet 2014 may be a direction from the air purification device 2200 to the inside of the medical cabin. The second outlet 2016 may be in flow communication with the outside of the medical cabin, and a second air flow direction of the second air outlet 2016 may be a direction from the air purification device 2200 to the outside of the medical cabin. The first air outlet 2214 and the second air outlet 2216 may be controlled by their respective air flow direction control devices.

In some embodiments, the housing 2210 may be provided with a second air inlet in flow communication with the outside of the medical cabin, so as to facilitate the air from outside the medical cabin to enter the medical cabin. For example, when the second air outlet 2016 is opened, the air in the medical cabin may be discharged out of the medical cabin. When a negative pressure is formed in the medical cabin, the second air inlet may be opened to allow fresh air outside the medical cabin to enter the air purification device 2200 through the second air inlet. After being filtered and/or disinfected, the fresh air may be transported to the medical cabin, so as to realize the air exchange inside and outside the medical cabin. Due to the introduction of fresh air from outside the medical cabin, the air quality inside the medical cabin can be further improved.

FIG. 23 is a block diagram illustrating an exemplary air purification system according to some embodiments of the present disclosure. A control system 2300 of an air purification device may include a control device 2310, a terminal device 2320, a disinfection device 2330, and a draught fan 2340. The control device 2310 may be connected with the terminal device 2320, the disinfection device 2330, and/or the draught fan 2340 via a wired or wireless connection. The terminal device 2320 (e.g., the terminal device 130) may generate a control instruction based on an input of a user and transmit the control instruction to the control device 2310. The control device 2310 may control the disinfection device 2330 and/or the draught fan 2340 based on the control instruction. For example, the control device 2310 may control a rotating rate of the draught fan 2340. Specifically, the rotating rate of the draught fan 2340 may be set to different gears, and the user may select the corresponding gear by manipulating the control device 2310 to control the air circulation speed of the air purification device. As another example, the control device 2310 may control to turn on or off the disinfection device 2330.

FIGS. 24A and 24B are schematic diagrams illustrating an exemplary in-vehicle medical system from different perspectives according to some embodiments of the present disclosure. As illustrating in FIG. 24, an in-vehicle medical system 2400 (also referred to as a movable medical system) may include a vehicle head 2410 and a carrying portion 2420 connected with the vehicle head 2410. A medical system 2500 may be arranged on the carrying portion 2420. The medical system 2500 may include a medical cabin 2510 and an electrical room 2540. The medical cabin 2510 may include an examination room 2520 and an operating room 2530.

The examination room 2520 may be configured to accommodate medical resources such as a medical device 2522, a couch 2524, etc. In some embodiments, the medical device 1522 may include any medical device as described above (e.g., FIGS. 1 to 9, etc.). For example, the medical device

1522 may include an imaging device such as a CT device, an MRI device, a DR device, etc. In some embodiments, the examination room 2520 may be isolated by a protective layer 2512, such as a lead protective layer, to prevent radiation rays generated by the medical device 2522 from leaking from the examination room 2520 to the operating room 2530, the vehicle head 2410, and/or the outside of the in-vehicle medical system 2400. In some embodiments, the examination room 2520 may be arranged in the vehicle head 2410 or any appropriate position in the medical cabin 2510.

The operating room 2530 may be equipped with a console configured to control the medical device 2522 (e.g., control a CT device to perform imaging scans on patents). In some embodiments, the operating room 2530 may be set independently of the examination room 2520.

The electrical room 2540 may be configured to provide electricity power to the examination room 2520 and/or the operating room 2530. In some embodiments, the electrical room 2540 may be arranged below the rear of the medical cabin 2510 and away from the examination room 2520, so that unnecessary influences on the examination room 2520 caused by electrical devices in the electrical room 2540 can be reduced. For example, the electrical devices may product noises, vibrations, etc., during operation. The electrical room 2540 may be arranged outside the examination room 2520 to reduce the interference of noises and/or vibrations on the examination room 1520. In some embodiments, the in-vehicle medical system 2400 may further include a power generator 2545 that is independent of an alternator provided in the vehicle head 2410. The power generator 2545 may be arranged in the electrical room 2540 configured to provide electrical energy for loads (e.g., the medical device 2522, the console, etc.) of the in-vehicle medical system 2400.

In some embodiments, one or more air purification devices as described in FIG. 20 may be arranged inside or outside the medical cabin 2520. In some embodiments, the one or more air purification devices may be arranged on one or more surfaces of the medical cabin 2520. For example, a first air purification device may be arranged on the top surface of the medical cabin 2510, a second air purification device may be arranged on the bottom surface of the medical device. As another example, the first air purification device and the second air purification device may be arranged on different sidewalls. In some embodiments, the air purification device may be arranged on the medical cabin 2520 via a fixing device (e.g., the fixing device 2050 illustrated in FIG. 20). In some embodiments, the fixing device may include a base, a hoisting structure, etc. The base may be placed on, for example, the bottom surface of the medical cabin 2520 to support the air purification device. The hoisting structure may be set on, for example, the top surface of the medical cabin 2520 to suspend the air purification device. In some embodiments, the fixing device may include a movable structure. The air purification device may be easily moved to any designed position in the medical cabin 2520 through the movable structure. In some embodiments, the air purification device(s) may be powered by the power generator 2545.

In some embodiments, one or more air quality sensors (e.g., air quality sensors 2552, 2554, and 2556) may be provided in the medical cabin 2520. For example, the air quality sensor(s) may be arranged on the same or different inner surfaces of the medical cabin 2510. Each air quality sensor may be configured to obtain one or more air quality parameters of the air in the medical cabin 2520 and estimate the air quality inside the medical cabin 2520 (e.g., the examination room 2520 and/or the operating room 2530). In some embodiments, the air quality parameters may include a formaldehyde content, an oxygen content, a carbon dioxide content, a carbon monoxide content, a sulfur dioxide content, or the like, or any combination thereof. In some embodiments, each of the air quality sensor(s) may be connected with a control device as described in FIG. 23. The control device may control one or more draught fans and/or one or more disinfection devices in each air purification device based on the air quality parameters and/or the air quality. For example, the control device may obtain the air quality parameters and/or the air quality from the air quality sensor(s) and generate a control instruction to control a draught fan and a disinfection device to turn on/off and operate according to the obtained air quality parameters and/or the air quality. Specifically, when the air quality parameters and/or the air quality is less than a threshold value, the control device may generate a turning on instruction to turn on at least one of the disinfection devices (e.g., the ultraviolet disinfection device 2122, the ozone disinfection device 2124).

It should be noted that to facilitate the manipulation, the control device of the air purification device(s) can be arranged on the inner side wall of the operating room 2530 or the examination room 2520, so that a medical staff in the operating room 2530 or the doctors and patients in the examination room 2520 can control the operating room 2530 to control the operation of the air purification device.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A medical device, comprising:
   a gantry including a bore configured to accommodate an object for scan;
   a table configured to support the object and move the object into the bore; and
   one or more disinfection devices configured for disinfection, wherein
   at least one of the one or more disinfection devices is arranged on the gantry; and
   a housing of the gantry is provided with a door to allow a disinfection medium of the at least one of the one or more disinfection devices to pass through when the door is in an open state, so that the disinfection medium of the at least one of the one or more disinfection devices directly pass through the door to disinfect the bore.

2. The medical device of claim 1, wherein at least one of the one or more disinfection devices is foldable or retractable.

3. The medical device of claim 1, wherein at least one of the one or more disinfection devices is arranged on the housing of the gantry, a component supported by the gantry, or the table.

4. The medical device of claim 3, wherein the bore includes a first opening and a second opening, and the at least one of the one or more disinfection devices is arranged at an end portion of the housing having the first opening or the second opening.

5. The medical device of claim 3, wherein the at least one of the one or more disinfection devices is arranged at a position of the housing corresponding to a top or bottom end of the bore.

6. The medical device of claim 1, wherein the disinfection medium of the at least one of the one or more disinfection devices penetrates the housing to the bore; and
at least a part of the housing is made of one of quartz glass, polymethyl methacrylate, and polycarbonate.

7. The medical device of claim 1, further comprising:
a table controller configured to control the table to move into the bore after at least one of the one or more disinfection devices performs disinfection for a preset time period.

8. The medical device of claim 1, wherein the medical device further includes a radiation source and a detector mounted on the gantry, the housing of the gantry forms a cavity configured to accommodate the radiation source and the detector, and at least one of the one or more disinfection devices is located in the cavity.

9. The medical device of claim 8, wherein the medical device further comprises an air inlet and an air outlet both arranged on the housing, wherein at least one of the air inlet or the air outlet is provided with one or more filtering devices in the cavity.

10. The medical device of claim 1, further comprising:
a monitoring device configured to acquire monitoring information associated with at least one of the medical device or the object; and
a control device configured to prevent at least one of the one or more disinfection devices from disinfecting the medical device in response to the monitoring information indicating that at least one object is within a preset range of the medical device.

11. The medical device of claim 1, further comprising:
an acquisition module configured to acquire information associated with at least one of the medical device or the object; and
a control device configured to:
determine that the medical device needs to be disinfected when the information associated with the at least one of the medical device or the object satisfies a compliance condition; and
generate a control instruction in response to determining that the medical device needs to be disinfected, wherein the control instruction includes a scan control instruction for restricting at least part of functions of the medical device to work.

12. The medical device of claim 11, wherein the control device is further configured to control at least one of the one or more disinfection devices to perform disinfection in response to receiving a disinfection instruction generated based on an input by a user that instructs to perform disinfection.

13. The medical device of claim 11, wherein the information associated with the at least one of the medical device or the object includes a scanning image of the object, medical information of the object, a state of the medical device, user information around the medical device; the medical information of the object includes a temperature; and at the user information around the medical device includes temperatures of objects in a surrounding environment of the medical device.

14. The medical device of claim 11, wherein
if the information associated with the at least one of the medical device or the object includes temperatures of one or more object, the compliance condition includes that at least one of the objects has a temperature greater than a temperature threshold;
if the information associated with the at least one of the medical device or the object includes an image or audio associated with a range of the medical device, the compliance condition is that the image and/or audio include information indicating that the object has a cough or fever.

15. The medical device of claim 1, wherein the at least one of the one or more disinfection devices is rotatably arranged, and the at least one of the one or more disinfection devices is directed toward different filtering devices at different times.

16. The medical device of claim 1, wherein at least one of the one or more disinfection devices and at least one of multiple filtering devices are arranged in a cavity formed by a housing of the medical device, and different disinfection devices have different orientations.

17. The medical device of claim 1, wherein if the at least one of the one or more disinfection devices arranged on the gantry is in a standby state, the door on the housing is closed.

18. The medical device of claim 1, wherein the door includes one or more grooves and one or more door panels, if the door panels extend out the grooves, the door is closed, and if the door panels retract into the grooves, the door is opened.

19. An air purification device arranged in a medical system including a medical cabin configured to accommodate medical resources, comprising:
one or more draught fans;
one or more air inlets;
one or more filtering devices;
one or more disinfection devices; and
one or more air outlets; wherein
at least one of the one or more filtering devices and at least one of the one or more disinfection devices are arranged between at least one of the one or more air inlets and at least one of the one or more air outlets, wherein
the air purification device is connected with a control device configured to control the air purification device, and the control device realizes automatic control according to an opening frequency of a door of the medical cabin.

20. A medical system including a medical cabin configured to accommodate medical resources, the medical cabin including an operating room and an examination room equipped with a medical device, at least one of the operating room or the examination room being equipped with an air purification device, wherein the air purification device includes:
one or more draught fans;
one or more air inlets;
one or more filtering devices;
one or more disinfection devices; and
one or more air outlets; wherein
at least one of the one or more filtering devices and at least one of the one or more disinfection devices are arranged between at least one of the one or more air inlets and at least one of the one or more air outlets, wherein
the air purification device is connected with a control device configured to control the air purification device, and the control device realizes automatic control according to an opening frequency of a door of the medical cabin.

\* \* \* \* \*